(12) United States Patent
Nielsen et al.

(10) Patent No.: US 6,352,851 B1
(45) Date of Patent: Mar. 5, 2002

(54) GLUCOAMYLASE VARIANTS

(75) Inventors: Bjarne Roenfeldt Nielsen, Virum; Allan Svendsen, Birkeroed; Henrik Pedersen, Odense; Jesper Vind, Lyngby; Hanne Vang Hendriksen, Holte; Torben Peter Frandsen, Frederiksberg, all of (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 09/351,814

(22) Filed: Jul. 12, 1999

Related U.S. Application Data
(60) Provisional application No. 60/093,528, filed on Jul. 21, 1998, and provisional application No. 60/115,545, filed on Jan. 12, 1999.

(30) Foreign Application Priority Data

Jul. 15, 1998 (DK) ......................................... 1998 00937
Dec. 17, 1998 (DK) ......................................... 1998 01667

(51) Int. Cl.⁷ ................................................. C12N 9/34
(52) U.S. Cl. ...................... 435/205; 435/183; 435/200; 435/202; 435/203
(58) Field of Search ................................ 435/183, 200, 435/205, 202, 203

(56) References Cited

FOREIGN PATENT DOCUMENTS

| | | |
|---|---|---|
| WO | WO 92/00381 | 1/1992 |
| WO | WO 98/03639 | 1/1998 |

OTHER PUBLICATIONS

Aleshin et al., Biochemistry, vol. 35, pp. 8319–8328 (1996).
Yao–Ting Yu and Gao–Xiang Li, Program sheet for *Enzyme Engineering XIV* at the Holiday Inn Lido Beijing, Beijing, China, Oct. 12–17, 1997.
Sierks et al., Protein Engineering, vol. 3, pp. 193–198 (1990).
Sierks et al., Protein Engineering, vol. 2, pp. 621–625 (1989).
Li et al., Protein Engineering, vol. 10, pp. 1199–1204 (1997).
Fierobe et al., Biochemistry, vol. 35, pp. 8696–8704 (1996).
Svensson et al., Karlsberg Res. Commun., vol. 48, pp. 529–544 (1983).
Berland et al., Biochemistry, vol. 34, pp. 10153–10161 (1995).
Frandsen et al., Biochemistry, vol. 34, pp. 10162–10169 (1995).
Chen et al., Protein Engineering, vol. 9, pp. 499–505 (1996).
Chen et al., Biochem. J., vol. 301, pp. 275–281 (1994).
Harris et al., Biochemistry, vol. 32, pp. 1618–1626 (1993).
Frandsen et al., Biochemistry, vol. 33, pp. 13808–13816 (1994).
Svensson et al., Eur. J. Biochem., vol. 154, pp. 497–502 (1986).
Aleshin et al., The Journal of Biological Chemistry, vol. 267, Issue of Sep. 25, pp. 19291–19298 (1992).
Chen et al., Protein Engineering, vol. 8, pp. 575–582 (1995).
Abstract of article: Mutational modulation of substrate bond–type specificity and thermostability of glucoamylase from *Aspergillus awamori* by replacement with short homologue active site sequences and thiol/disulfide engineering, Biochem., vol. 35, pp. 8696–8704 (1996).
Abstract of article: Identification and elimination by site–directed mutagenesis of thermoabile aspartyl bonds in *Aspergillus awamori* glucoamylase, Protein England, vol. 8, pp. 575–582 (1995).

*Primary Examiner*—Rebecca E. Prouty
*Assistant Examiner*—Manjunath N. Rao
(74) *Attorney, Agent, or Firm*—Elias Lamiris Esq.; Jason Garbell Esq.

(57) ABSTRACT

The invention relates to a variant of a parent fungal glucoamylase, which exhibits improved thermal stability and/or increased specific activity using saccharide substrates.

6 Claims, 1 Drawing Sheet

GLUCOAMYLASE VARIANTS

CROSS-REFERENCE TO RELATED APPLICATIONS

This application claims priority under 35 U.S.C. 119 of Danish application Nos. PA 1998 00937 and PA 1998 01667 filed Jul. 15, 1998 and Dec. 17, 1998 and U.S. provisional application Nos. 60/093,528 and 60/115,545 filed Jul. 21, 1998 and Jan. 12, 1999, the contents of which are fully incorporated herein by reference.

FIELD OF THE INVENTION

The present invention relates to novel glucoamylase variants (mutants) of parent AMG, in particular with improved thermal stability and/or increased specific activity suitable for, e.g., starch conversion, e.g., for producing glucose from starch. More specifically, the present invention relates to glucoamylase enzyme variants and the use of such variant enzymes.

BACKGROUND OF THE INVENTION

Glucoamylase (1,4-α-D-glucan glucohydrolase, EC 3.2.1.3) is an enzyme which catalyzes the release of D-glucose from the non-reducing ends of starch or related oligo- and polysaccharide molecules. Glucoamylases are produced by several filamentous fungi and yeasts, with those from Aspergillus being commercially most important.

Commercially, the glucoamylase enzyme is used to convert corn starch which is already partially hydrolyzed by an α-amylase to glucose. The glucose is further converted by glucose isomerase to a mixture composed almost equally of glucose and fructose. This mixture, or the mixture further enriched with fructose, is the commonly used high fructose corn syrup commercialized throughout the world. This syrup is the world's largest tonnage product produced by an enzymatic process. The three enzymes involved in the conversion of starch to fructose are among the most important industrial enzymes produced.

One of the main problems that exist with regard to the commercial use of glucoamylase in the production of high fructose corn syrup is the relatively low thermal stability of glucoamylase. Glucoamylase is not as thermally stable as α-amylase or glucose isomerase and it is most active and stable at lower pH's than either α-amylase or glucose isomerase. Accordingly, it must be used in a separate vessel at a lower temperature and pH.

Glucoamylase from *Aspergillus niger* has a catalytic (aa 1–') and a starch binding domain (aa 509–616) separated by a long and highly O-glycosylated linker (Svensson et al. (1983), *Carlsberg Res. Commun.* 48, 529–544, 1983 and (1986), *Eur. J. Biochem.* 154, 497–502). The catalytic domain (aa 1–471) of glucoamylase from *A. awamori* var. X100 adopt an $(\alpha/\alpha)_6$-fold in which six conserved α→α loop segments connect the outer and inner barrels (Aleshin et al. (1992), *J. Biol.Chem.* 267, 19291–19298). Crystal structures of glucoamylase in complex with 1-deoxynojirimycin (Harris et al. (1993), *Biochemistry*, 32, 1618–1626) and the pseudotetrasaccharide inhibitors acarbose and D-gluco-dihydroacarbose (Aleshin et al. (1996), *Biochemistry* 35, 8319–8328) furthermore are compatible with glutamic acids 179 and 400 acting as general acid and base, respectively. The crucial role of these residues during catalysis have also been studied using protein engineering (Sierks et al. (1990), *Protein Engng.* 3, 193–198; Frandsen et al. (1994), *Biochemistry*, 33, 13808–13816).

Glucoamylase-carbohydrate interactions at four glycosyl residue binding subsites, −1, +1, +2, and +3 are highlighted in glucoamylase-complex structures (Aleshin et al. (1996), *Biochemistry* 35, 8319–8328) and residues important for binding and catalysis have been extensively investigated using site-directed mutants coupled with kinetic analysis (Sierks et al. (1989), *Protein Engng.* 2, 621–625; Sierks et al. (1990), *Protein Engng.* 3, 193–198; Berland et al. (1995), *Biochemistry*, 34, 10153–10161; Frandsen et al. (1995), *Biochemistry*, 34, 10162–10169.

Different substitutions in *A. niger* glucoamylase to enhance the thermal stability have been described: i) substitution of α-helical glycines: G137A and G139A (Chen et al. (1996), *Prot. Engng.* 9, 499–505); ii) elimination of the fragile Asp-X peptide bonds, D257E and D293E/Q (Chen et al. (1995), *Prot. Engng.* 8, 575–582); prevention of deamidation in N182 (Chen et al. (1994), *Biochem. J.* 301, 275–281); iv) engineering of additional disuiphide bond, A246C (Fierobe et al. (1996), *Biochemistry*, 35, 8698–8704; and v) introduction of Pro residues in position A435 and S436 (Li et al. (1997), *Protein Engng.* 10, 1199–1204. Furthermore Clark Ford presented a paper on Oct. 17, 1997, ENZYME ENGINEERING 14, Beijing/China Oct. 12–17, 1997, Abstract number: Abstract book p. 0–61. The abstract suggests mutations in positions G137A, N20C/A27C, and S30P in a (not disclosed) *Aspergillus awamori* glucoamylase to improve the thermal stability.

Additional information concerning glucoamylase can be found on an Internet homepage (http://www.public.iastate.edu/~pedro/glase/glase.html) "Glucoamylase WWW page" (Last changed Aug. 10, 1997 ) by Pedro M. Coutinho discloses informations concerning glucoamylases, including glucoamylases derivable from Aspergillus strains.

Chemical and site-directed modifications in the *Aspergillus niger* glucoamylase are listed.

BRIEF DISCLOSURE OF THE INVENTION

The object of the present invention is to provide improved glucoamylase variants with improved thermostablility and/or increased specific activity suitable for use in, e.g., the saccharification step in starch conversion processes.

The term "a glucoamylase variant with improved thermostability" means in the context of the present invention a glucoamylase variant which has a higher $T_{1/2}$ (half-time) than the corresponding parent glucoamylase. The determination of T½ (Method I and Method II) is described below in the "Materials & Methods" section.

The term "a glucoamylase variant with increased specific activity" means in the context of the present invention a glucoamylase variant with increased specific activity towards the α-1,4 linkages in the saccharide in question. The specific activity is determined as $k_{cat}$ or AGU/mg (measured as described below in the "Materials & Methods" section). An increased specific activity means that the $k_{cat}$ or AGU/mg values are higher when compared to the $k_{cat}$ or AGU/mg values, respectively, of the corresponding parent glucoamylase.

The inventors of the present invention have provided a number of improved variants of a parent glucoamylase with improved thermostability and/or increased specific activity in comparison to the parent corresponding enzyme. The improved thermal stability is obtained by substituting selected positions in a parent glucoamylase. This will be described in details below.

NOMENCLATURE

In the present description and claims, the conventional one-letter and three-letter codes for amino acid residues are used. For ease of reference, glucoamylase variants of the invention are described by use of the following nomenclature:

Original amino acid(s):position(s):substituted amino acid(s)

According to this nomenclature, for instance the substitution of alanine for asparagine in position 30 is shown as:

Ala30Asn or A30N a deletion of alanine in the same position is shown as:

Ala30* or A30* and insertion of an additional amino acid residue, such as lysine, is shown as:

Ala30AlaLys or A30AK

A deletion of a consecutive stretch of amino acid residues, such as amino acid residues 30–33, is indicated as (30–33)* or Δ(A30–N33).

Where a specific glucoamylase contains a "deletion" in comparison with other glucoamylases and an insertion is made in such a position this is indicated as:

*36Asp or *36D for insertion of an aspartic acid in position 36

Multiple mutations are separated by plus signs, i.e.:

Ala30Asp+Glu34Ser or A30N+E34S representing mutations in positions 30 and 34 substituting alanine and glutamic acid for asparagine and serine, respectively. Multiple mutation may also be separated as follows, i.e., meaning the same as the plus sign:

Ala30Asp/Glu34Ser or A30N/E34S

When one or more alternative amino acid residues may be inserted in a given position it is indicated as A30N,E or A30N/E, or A30N or A30E Furthermore, when a position suitable for modification is identified herein without any specific modification being suggested, it is to be understood that any amino acid residue may be substituted for the amino acid residue present in the position. Thus, for instance, when a modification of an alanine in position 30 is mentioned, but not specified, it is to be understood that the alanine may be deleted or substituted for any other amino acid, i.e., any one of:

R,N,D,A,C,Q,E,G,H,I,L,K,M,F,P,S,T,W,Y,V.

DETAILED DISCLOSURE OF THE INVENTION

Figure 1:
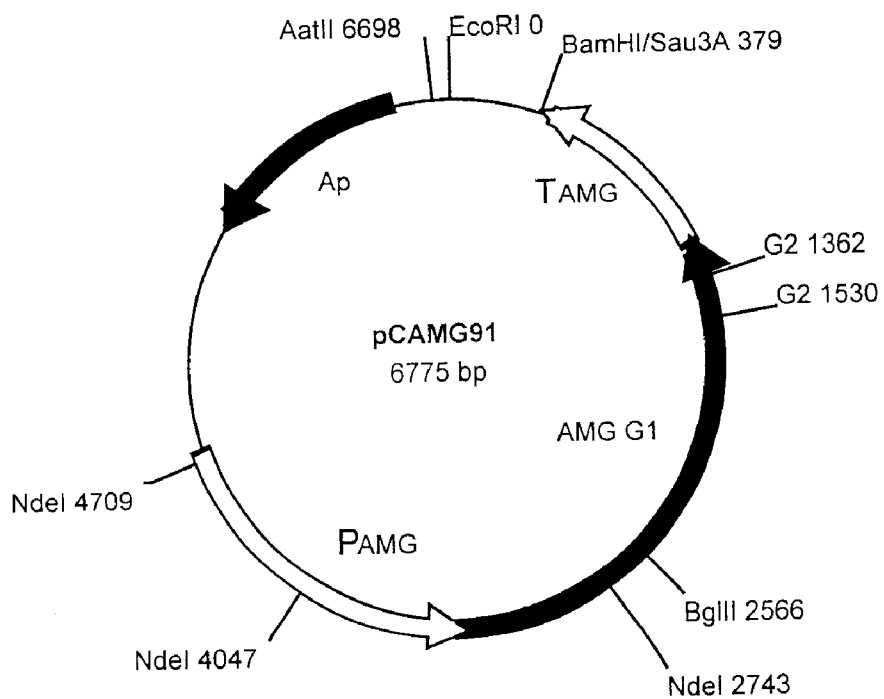
FIG. 1 shows the plasmid pCAMG91 containing the *Aspergillus niger* G1 glucoamylase gene.

A goal of the work underlying the present invention was to improve the thermal stability and/or increase the specific activity of particular glucoamylases which are obtainable from fungal organisms, in particular strains of the Aspergillus genus and which themselves had been selected on the basis of their suitable properties in starch conversion or alcohol fermentation.

Identifying Positions and/or Regions to be Mutated to Obtain Improved Thermostability and/or Increased Specific Activity Molecular dynamics (MD) simulations indicate the mobility of the amino acids in the protein structure (see McCammon, J A and Harvey, S C., (1987), "Dynamics of proteins and nucleic acids". Cambridge University Press.). Such protein dynamics are often compared to the crystallographic B-factors (see Stout, G H and Jensen, L H, (1989), "X-ray structure determination", Wiley). By running the MD simulation at different protonation states of the titrate able residues, the pH related mobility of residues are simulated. Regions having the highest mobility or flexibility (here isotropic fluctuations) are selected for random mutagenesis. It is here understood that the high mobility found in certain areas of the protein, can be thermally improved by substituting residues in these residues. The substitutions are directed against residues that will change the dynamic behaviour of the residues to e.g. bigger side-chains and/or residues which have capability of forming improved contacts to residues in the near environment. The AMG from *Aspergillus niger* was used for the MD simulation. How to carry out MD simulation is described in the Materials & Methods" section below.)

Regions found by Molecular dynamics (MD) simulations to be suitable for mutation when wanting to obtain improved thermal stability and/or increased specific activity are the following:

Region: 1–18,
Region: 19–35,
Region: 73–80,
Region: 200–212,
Region: 234–246,
Region: 334–341,
Region: 353–374,
Region: 407–411,
Region: 445–470, Regions found to be of interest for increasing the specific activity and/or improved thermostability are the regions in 1 proximity to the active site. Regions positioned in between the α-helixes, and which may include positions on each side of the N-and C-terminal of the α-helixes, at the substrate binding site is of importance for the activity of the enzyme. These regions constitute the following regions:

Region: 40–62,
Region: 93–127,
Region: 170–184,
Region: 234–246,
Region: 287–319,
Region: 388–414.

Rhizopus, Talaromyces, such as *Talaromyces emersonii* (dislosed in WO 99/28448), and Thielavia have high specific activity towards maltodextrins, including maltose and maltohepatose. Therefore, regions being of special interest regarding (transferring) increased specific activity are:

Region: 200–212,
Region: 287–300,
Region: 305–319.

The present inventors have found that it is in fact possible to improve the thermal stability and/or to increase the specific activity of a parent glucoamylase by modification of one or more amino acid residues of the amino acid sequence of the parent glucoamylase. The present invention is based on this finding.

Accordingly, in a first aspect the present invention relates to an improved variant of a parent glucoamylase comprising one or more mutations in the regions and positions described further below.

Parent Glucoamylases

Parent glucoamylase contemplated according to the present invention include fungal glucoamylases, in particular fungal glucoamylases obtainable from an Aspergillus strain, such as an *Aspergillus niger* or *Aspergillus awamori* glucoamylases and variants or mutants thereof, homologous glucoamylases, and further glucoamylases being structurally and/or functionally similar to SEQ ID NO: 2. Specifically contemplated are the *Aspergillus niger* glucoamylases G1 and G2 disclosed in Boel et al. (1984), "Glucoamylases G1 and G2 from *Aspergillus niger* are synthesized from two different but closely related mRNAs", EMBO J. 3 (5), p. 1097–1102. The G2 glucoamylase is disclosed in SEQ ID NO: 2. The G1 glucoamylase is disclosed in SEQ ID NO: 13. Another AMG backbone contemplated is *Talaromyces erersonii*, especially *Talaromyces emersonii* DSM disclosed in WO 99/28448 (Novo Nordisk).

Commercially Available Parent Glucoamylases

Commercially available parent glucoamylases include AMG from Novo Nordisk, and also glucoamylase from the companies Genencor, Inc. USA, and Gist-Brocades, Delft, The Netherlands.

Glucoamylase Variants

In the first aspect the invention relates to a variant of a parent glucoamylase comprising one or more mutation(s) in the following positions(s) or region(s) in the amino acid sequence shown in NO: 2:

Region: 1–18,
Region: 19–35,
Region: 40–62,
Region: 73–80,
Region: 93–127,
Region: 170–184,
Region: 200–212,
Region: 234–246,
Region: 287–319,
Region: 334–341,
Region: 353–374,
Region: 388–414,
Region: 445–470, and/or in a corresponding position or region in a homologous glucoamylase which displays at least 60% homology with the amino acid sequences shown in SEQ ID NO: 2, with the exception of the following substitutions: N20C, A27C, S30P, Y48W, Y50F, W52F, R54K/L, D55G/V, G57A, K108R, D112Y, Y116A/W, S119C/W/E/G/Y/P, W120H/L/F/Y, G121T/A, R122Y, P123G, Q124H, R125K, W170F, N171S, Q172N, T173G, G174C, Y175F, D176N/E, L177H/D, W178R/D, E179Q/D, E180D/Q, V181D/A/T, N182A/D/Q/Y/S, G183K, S184H, W212F, R241K, A246C, D293E/Q, A302V, R305K, Y306F, D309N/E, Y312W, W317F, E389D/Q, H391W, A392D, A393P, N395Q, G396S, E400Q/C, Q401E, G407D, E408P, L410F, S411A/G/C/H/D, S460P In an embodiment the region mutated is the Region: 1–18. Specific preferred positions contemplated include one or more of:

1,2,3,4,5,6,7,8,9,10,11,12,13,14,15,16,17,18.

Specific mutations include one or more of: A1V, T2P/Q/R/H/M/E/K, L3N, N9A, A11E/P, 118V.

Preferred combinations of mutations include one or more of:

A1V+L66R+Y402F+N427S+S486G,
T2K+S30P+N427M+S44G+V470M,
T2E+T379A+S386K+A393R,
T2Q+A11P+S394R,
T2R+L66V+S394P+Y402F
T2M+N9A+T390R+D406N+L410R,
T2R+S386R+A393R,
A11P+T2Q+S394R,
A11E+E408R,
I18V+T51S+S56A+V59T+L60A.

In an embodiment the region mutated is the Region: 19–35. Preferred sub-regions include one or more of: 21–26, 31–35.

Specific preferred positions contemplated include one or more of: 19, 21, 22, 23, 24, 25, 26, 28, 29, 31, 32, 33, 34, 35.

Specific mutations include one or more of: L19N, N20T, G23A, A24S/T, D25S/T/R, G26A, A27S/T, W28R/Y, S30T/N, G31A, A32V, D33R/K/H, S34N.

In an embodiment the region mutated is the Region: 40–62. Preferred sub-regions include one or more of: 40–47, 58–62.

Specific preferred positions contemplated include one or more of:

40,41,42,43,44,45,46,47,49,51,53,56,58,59,60,61,62.

Specific mutations include one or more of:

S40C/A/G,
T43R,
T51S/D,
T53D,
S56A/C,
V59T/A,
L60A.

Preferred combinations of mutations include one or more of:

T51S+S56A+V59T+L60A+I18V
V59A+A393R+T490A+PLASD(N-terminal extension).

In an embodiment the region mutated is the Region: 73–80.

Specific preferred positions contemplated include one or more of:

73,74,75,76,77,78,79,80.

Specific mutations include one or more of:

S73P/D/T/N/Q/E,
L74I/D,
L75A/R/N/D/C/Q/E/G/H/I/K/M/P/S/T/V, preferred are I/N/D,
S76A/R/N/D/C/Q/E/G/H/I/L/K/F/M/P/S/T/W/Y/V, preferred T/A)
T77V/T,
I78V,
E79A/R/N/D/C/Q/G/H/I/L/K/F/M/P/S/T/Y/V, preferred are Q/R/K)
N80A/R/D/C/Q/E/G/H/I/L/K/F/M/P/S/T/W/Y/V, preferred are
H/D/E/R/K/T/S/Y.

In an embodiment the region mutated is the Region: 93–127. In an additional embodiment the sub-region is: Region: 93–124. Preferred sub-regions include one or more of: 93–107, 109–111, 113–115.

Specific preferred positions contemplated include one or more of:

93,94,95,96,97,98,99,100,101,102,103,104,105,106,109, 110,111,113, 114,115,117,118,126,127.

Specific mutations include one or more of: N93T,
94V,
S95N,
D97S,
L98S/P,

S100T/D,
A102S/*,
P107M/L/A/G/S/T/V/I,
N110T,
V111P,
D112N,
E113M/A,
T114S,
A115Q/A,
Y116F,
S119A/R/N/D/Q/H/I/L/K/F/M/T/V, preferred is A,
R122A/N/D/C/Q/E/G/H/I/L/K/F/M/P/S/T/W/V,
G127A.

Preferred combinations of mutations include one or more of:
S119P+G447S,
S119P+Y402F,
S119P+A393R,
S119P+I189T+223F+F227Y+Y402F
S119P+T416H+Y402F+Y312Q.

In an embodiment the region mutated is the Region: 170–184.
Specific mutations include one or more of:
N171R/K/Q/E/W/F/Y,
Q172A/R/N/D/C/E/G/H/I/L/K/F/M/P/S/T/W/Y/V,
T173K/R/S/N/Q,
G174A,S,
Y175N/Q/D/E,
D176L
L177I
E180N/M
V181I/T
N182R/C/E/G/H/I/L/K/M/P/T/W/Y/V.
G183A
S184D/N/E/Q/L/I/T/R/K.

In an embodiment the region mutated is the Region: 200–212. Preferred sub-regions include: 200–211.
Specific preferred positions contemplated include one or more of:
200,201,202,203,204,205,206,207,208,209,210,211.
Specific mutations include one or more of: A201D, F202L, A203L, T204K, A205R/S, V206L/N, G207N, S208H/T/D, S209T, S211P, W212N/A/T.

In an embodiment the region mutated is the Region: 234–246. Preferred sub-regions include one or more of: 234–240, 242–245.
Specific preferred positions contemplated include one or more of:
234,235,236,237,238,239,240,242,243,244,245.
Specific mutations include one or more of:
L234A/R/N/D/C/Q/E/G/H/I/K/M/F/P/S/T/W/Y/V.
A235S
F237Y/H/N/D.
D238T/S.
S239A/R/N/D/C/G/H/I/L/F/P/S/T/Y/V.
S240G
S242S/P/T/A/Y/H/N/D.
G243S/P/T/A/Y/H/N/D.
K244R,
A246T.

Preferred combinations of mutations include one or more of:
A246T+T72I.

In an embodiment the region mutated is the Region: 287–319. Preferred sub-regions include one or more of: 287–292, 294–301, 313–316.
Specific preferred positions contemplated include one or more of:
287,288,289,290,291,292,294,295,296,297,298,299,300, 301,
303,307,308,310,311,313,314,315,316,318,319.
Specific mutations include one or more of:
S287A/R/N/D/C/Q/E/G/H/I/L/K/M/T/V,
I288L/N/Q,
Y289F,
T290A/R/N/D/C/Q/E/G/H/I/L/K/M/P/S/V,
L291I/D/N,
292D,
D293A/R/N/C/Q/E/G/H/I/L/K/M/S/T/V,
G294A/R/N/D/C/Q/E/H/I/L/K/M/P/S/T/V,
L295A/R/N/D/C/Q/E/G/H/K/M/S/T/V,
S296A/R/N/D/C/Q/E/G/H/I/L/K/M/T/V,
D297A/R/N/C/Q/E/G/H/I/L/K/M/P/S/T/V,
S298A/R/N/D/C/Q/E/G/H/I/L/K/F/M/T/V,
E299A/R/N/D/C/Q/G/H/I/L/K/M/S/T/V.
V301T/I,
A302R/N/D/C/Q/E/G/H/I/L/K/F/M/P/S/T/W/Y/V/, preferred S,
V303T/I,
G304A,
R305A/N/D/C/Q/E/G/H/I/L/F/M/P/S/T/W/Y/V,
Y306A/R/N/D/C/Q/E/G/H/I/L/K/M/P/S/T/W/V.
E308A/R/N/D/C/Q/G/H/I/L/K/M/P/S/T/V, preferred Q,
D309L,
T310V/S,
Y311N,
Y312Q/N,
N313T/S/G
N315Q/E/R,
F318A/R/N/D/C/Q/E/G/H/I/L/K/M/P/S/T/W/Y/V, preferred is Y.

Preferred combinations of mutations include one or more of:
Y312Q+S119P+T416H+Y402F,
Y312Q+S119P+Y402F+T416H+S411V,
Y312Q+T416H
N313G+F318Y.

In an embodiment the region mutated is the Region: 334–341.
Specific preferred positions contemplated include one or more of:
334,335,336,337,338,339,340,341.
Specific mutations include one or more of:
D336A/R/N/C/Q/E/G/H/I/L/K/M/F/P/S/T/W/Y/V.
K337A/R/N/D/C/Q/E/G/H/I/L/M/F/P/S/T/W/Y/V.
Q338A/R/N/D/C/G/H/I/L/F/P/S/T/Y/V.
G339S/P/T/A.
S340I/T/N/V/A/D/G.
L341F/L/I/V.

Preferred combinations of mutations include one or more of:
S340G+D357S+T360V+S386P.

In an embodiment the region mutated is the Region: 353–374.
Specific preferred positions contemplated include one or more of:
353,354,355,356,357,358,359,360,361,362,363,364,365, 366,367,368,369,370,371,372,373,374.
Specific mutations include one or more of:
A353D/S,
S356P/N/D,
D357S,
A359S,
T360V,
G361S/P/T/A,
T362R,
S364A/R/N/D/C/Q/E/G/H/I/L/K/M/E/P/T/W/Y/V,
S365A/R/N/D/C/Q/E/G/H/I/L/K/M/T/P/T/W/Y/V,
S366T,
S368P/T/A,
T369A/R/N/D/C/Q/E/G/H/I/L/K/M/F/P/T/W/Y/V,
S371Y/H/N/D,
S372F/Y/C/L/P/H/R/I/T/N/S/V/A/D/G.
Preferred combinations of mutations include one or more of:
S3562+S366T,
D357S+T360V+S371H.
D357S+T360V+S386P+S340G.
In an embodiment the region mutated is the Region: 388–414. Preferred sub-regions include one or more of: 397–399,402–406, 412–414.
Specific preferred positions contemplated include one or more of:
388,389,390,394,397,398,399,402,403,404,405,406,409, 412,413,414.
Specific mutations include one or more of: T390R,
A393R,
S394P/R,
M398L,
S399A/R/N/D/C/Q/E/G/H/I/L/K/F/M/P/T/W/Y/V, preferred are T/Q/C,
Y402A/R/N/D/C/Q/E/G/H/I/L/K/F/M/P/S/T/V, preferred is F,
D403S,
S405T,
D406N,
E408C/R,
A409R/N/D/C/Q/E/G/H/I/L/K/F/M/P/S/T/W/Y/V, preferred is P,
L410R/I,
S411R/N/Q/E/I/L/K/F/M/P/T/W/Y/V, preferred is V,
A412C,
R413A/N/D/C/Q/E/G/H/I/L/K/F/M/P/S/T/W/Y/V.
D414A.
Preferred combinations of mutations include one or more of:
A393R+T490A+V59A+PLASD(N-terminal extension)
S394R+T2Q+A11P,
Y402F+S411V,
Y402F+S411V+S119P
Y402F+S411V+S119P+A393R,
Y402F+Y312Q+S119P+T416H,
E408R+S386N,
E408R+A425T+S465P+T494A,
L410R+A393R,
Y402F+Y312Q+S119P+T416H+S411V+A393R.
In an embodiment the region mutated is the Region: 445–470. Preferred sub-regions include one or more of: 445–459, 461–470.
Specific preferred positions contemplated include one or more of:
445,446,447,448,449,450,451,452,453,454,455,456,457, 458,459,461, 462,463,464,465,466,467,467,468,469, 470.
Specific mutations include one or more of: G447S,G456C/ P,S465P.
Specific variants include variants having one or more of the following substitutions: A1V, T2E/P/Q/R/H/M, L3P/N, N9A, A11P/E, I18V, L19N, N20T, G23A, A24S/T, D25S/T/R, G26A, A27S/T, W28R/Y, S30T/N, G31A, A32V, D33R/K/H, S34N, S40C, T43R, T51D/S, T53D, S56A/C, V59T/A, L60A, N93T, P94V, S95N, D97S, L98P/S, S100T/D, A102S/*, N110T, V111P, D112N, E113M/A, T114S, A115Q/G, Y116F, S119A, G127A, N182E, A201D, F202L, A203L, T204K, A205R/S, V206L/N, G207N, S208H/T/D, S209T, S211P, W212N/A/T, A246T Y312Q, N313T/S/G, A353D/S, S356P/N/D, D357S, A359S, T360V, G361S/P/T/A, T362R, S364A/R/N/D/C/Q/E/G/H/I/L/K/M/F/P/T/W/Y/V, S365A/R/N/D/C/Q/E/G/H/I/L/K/M/F/P/T/W/Y/V, S366T, S368P/T/A, T369A/R/N/D/C/Q/E/G/H/I/L/K/M/F/P/T/W/Y/V, S371Y/H/N/D, S372F/Y/C/L/P/H/R/I/T/N/S/V/A/D/G, T390R, A393R, S394R/P, M398L, S399C/Q/T, Y402F, D403S, S405T, D406N, E408C/R, L410I/R, S411V, A412C, D414A, G447S, S465P.

Improved Thermal Stability

In a second aspect the invention relates to a variant of a parent glucoamylase with improved thermal stability, in particular in the range from 40–80° C., preferably 60–80° C., and preferably at pH 4–5, said variant comprising one or more mutation(s) in the following position(s) or region(s) in the amino acid sequence shown in NO: 2:
Region: 1–18,
Region: 19–35,
Region: 73–80,
Region: 93–127,
Region: 170–184,
Region: 200–212,
Region: 234–246,
Region: 287–319,
Region: 334–341,
Region: 353–374,
Region: 388–414,
Region: 445–470,
and/or in a corresponding position or region in a homologous glucoamylase which displays at least 60% homology with the amino acid sequences shown in SEQ ID NO: 2, with the exception of the following substitutions: N20C, A27C, S30P, A246C.

As substrate binding may improve the stability region 93–127, Region: 170–184, Region: 305–319 are also contemplated for thermostabilization according to the present invention.

In an embodiment the region mutated is the Region: 1–18. Specific preferred positions contemplated include one or more of:
1,2,3,4,5,6,7,8,9,10,11,12,13,14,15,16,17,18.

Specific mutations include one or more of: A1V, T2P/Q/R/H/M/E, N9A, A11E/P.
Preferred combinations of mutations include one or more of:
A1V+L66R+Y402F+N427S+S486G,
T2K+S30P+N427M+S44G+V470M,
T2E+T379A+S386K+A393R,
T2R+S386R+A393R,
A11P+T2Q+S394R,
T2Q+A11P+S394R,
T2R+L66V+S394P+Y402F,
T2M+N9A+T390R+D406N+L410R,
T2R+S386R+A393R,
A11E+E408R.

In an embodiment the region mutated is the Region: 19–35. Preferred sub-regions include one or more of: 21–26, 31–35.
Specific preferred positions contemplated include one or more of:
19,21,22,23,24,25,26,28,29,31,32,33,34,35.
Specific mutations include one or more of: L19N, N20T, G23A, A24S/T, D25S/T/R, G26A, A27S/T, W28R/Y, S30T/N, G31A, A32V, D33R/K/H, S34N.

In an embodiment the region mutated is the Region: 73–80.
Specific preferred positions contemplated include one or more of:
73,74,75,76,77,78,79,80.
Specific mutations include one or more of:
S73P/D/T/N/Q/E,
L74I/D,
L75A/R/N/D/C/Q/E/G/H/I/K/M/P/S/T/V, preferred are I/N/D,
S76A/R/N/D/C/Q/E/G/H/I/L/K/F/M/P/S/T/W/Y/V, preferred T/A)
T77V/T,
I78V,
E79A/R/N/D/C/Q/G/H/I/L/K/F/M/P/S/T/Y/V, preferred are Q/R/K)
N80A/R/D/C/Q/E/G/H/I/L/K/F/M/P/S/T/W/Y/V, preferred are H/D/E/R/K/T/S/Y.

In an embodiment the region mutated is the Region: 93–127. In an additional embodiment the sub-region is: Region: 93–124. Preferred sub-regions include one or more of: 93–107, 109–111, 113–115.
Specific preferred positions contemplated include one or more of:
93,94,95,96,97,98,99,100,101,102,103,104,105,106,109, 110,111,113, 114,115,117,118,126,127.
Preferred mutations include one or more of:
P107M/L/A/G/S/T/V/I,
S119A/R/N/D/Q/H/I/L/K/F/M/T/V, preferred is A,
R122A/N/D/C/Q/E/G/H/I/L/K/F/M/P/S/T/W/V,
Preferred combinations of mutations include one or more of:
S119P+G447S.
S119P+A393R.

In an embodiment the region mutated is the Region: 170–184.
Specific mutations include one or more of:
N171R/K/Q/E/W/F/Y,
Q172A/R/N/D/C/E/G/H/I/L/K/F/M/P/S/T/W/Y/V,
T173K/R/S/N/Q,
G174A,S,
Y175N/Q/D/E,
D176L
L177I
E180N/M
V181I/T
N182R/C/E/G/H/I/L/K/M/P/T/W/Y/V.
G183A
S184D/N/E/Q/L/I/T/R/K.

In an embodiment the region mutated is the Region: 200–212. Preferred sub-regions include: 200–211.
Specific preferred positions contemplated include one or more of:
200,201,202,203,204,205,206,207,208,209,210,211.
Specific mutations include one or more of: A203L, S211P.

In an embodiment the region mutated is the Region: 234–246. Preferred sub-regions include one or more of: 234–240, 242–245.
Specific preferred positions contemplated include one or more of:
234,235,236,237,238,239,240,242,243,244,245.
Specific mutations include one or more of:
L234A/R/N/D/C/Q/E/G/H/I/K/M/F/P/S/T/W/Y/V,
A235S,
F237Y/H/N/D,
D238T/S,
S239A/R/N/D/C/G/H/I/L/F/P/S/T/Y/V,
S240G,
S242S/P/T/A/Y/H/N/D,
G243S/P/T/A/Y/H/N/D,
K244R,
A246T.
Preferred combinations of mutations include one or more of:
A246T+T72I.

In an embodiment the region mutated is the Region: 287–319. Preferred sub-regions include one or more of: 287–292, 294–301, 313–316.
In an additional embodiment the sub-region include: 305–319.
Specific preferred positions contemplated include one or more of:
287,288,289,290,291,292,294,295,296,297,298,299,300, 301,302, 303,307,308,310,311,313,314,315,316,318, 319.
Specific mutations include one or more of:
Y312Q,
F318A/R/N/D/C/Q/E/G/H/I/L/K/M/P/S/T/W/Y/V, preferred is Y.
Preferred combinations of mutations include one or more of:
N313G+F318Y,
Y302Q+S119P+T416H+Y402F.

In an embodiment the region mutated is the Region: 334–341.
Specific preferred positions contemplated include one or more of:
334,335,336,337,338,339,340,341.
Specific mutations include one or more of:
D336A/R/N/C/Q/E/G/H/I/L/K/M/F/P/S/T/W/Y/V.
K337A/R/N/D/C/Q/E/G/H/I/L/M/F/P/S/T/W/Y/V.
Q338A/R/N/D/C/G/H/I/L/F/P/S/T/Y/V.
G339S/P/T/A.

S340I/T/N/V/A/D/G.

L341F/L/I/V.

Preferred combinations of mutations include one or more of:

S340G+D357S+T360V+S386P.

In an embodiment the region mutated is the Region: 353–374.

Specific preferred positions contemplated include one or more of:

353,354,355,356,357,358,359,360,361,362,363,364,365, 366,367,368, 369,370,371,372,373,374.

Specific mutations include one or more of:

A353D/S,

S356P/N/D,

D357S,

A359S,

T360V,

G361S/P/T/A,

T362R,

S364A/R/N/D/C/Q/E/G/H/I/L/K/M/F/P/T/W/Y/V,

S365A/R/N/D/C/Q/E/G/H/I/L/K/M/F/P/T/W/Y/V,

S366T,

S368P/T/A,

T369A/R/N/D/C/Q/E/G/H/I/L/K/M/F/P/T/W/Y/V,

S371Y/H/N/D,

S372F/Y/C/L/P/H/R/I/T/N/S/V/A/D/G.

Preferred combinations of mutations include one or more of:

S356P+S366T,

D357S+T360V+S371H

D357S+T360V+S386P+S340G.

In an embodiment the region mutated is the Region: 388–414. Preferred sub-regions include one or more of: 397–399,402–406, 412–414.

In an additional embodiment the sub-region is: 407–411

Specific preferred positions contemplated include one or more of:

388,389,390,394, 397,398,399,402,403,404,405,406,409, 412,413,414.

Specific mutations include one or more of: T390R,

A393R,

S394P/R,

S399A/R/N/D/C/Q/E/G/H/I/L/K/F/M/P/T/W/Y/V, preferred are T/Q/C,

Y402A/R/N/D/C/Q/E/G/H/I/L/K/F/M/P/S/T/V, preferred is F,

D403S,

S405T,

D406N,

E408C/R,

Q409A/R/N/D/C/E/G/H/I/L/K/F/M/P/S/T/W/Y/V, preferred is P,

L410I/R,

S411V,

A412C,

R413A/N/D/C/Q/E/G/H/I/L/K/F/M/P/S/T/W/Y/V.

D414A.

Preferred combinations of mutations include one or more of:

A393R+T2R+S386R,

A393R+T490A+V59A+PLASD(N-terminal extension),

S394R+T2Q+A11P,

Y402F+T2R+L66V+S394P,

Y402F+S411V+S119P

Y402F+S411V,

Y402F+312Q+S119P+T416H,

S411V+A393R,

E408R+S386N,

E408R+A425T+S465P+T494A,

L410R+A393R,

S411V+S119P+402F+A393R,

S411V+S119P+402F+A393R+T416H.

In an embodiment the region mutated is the Region: 445–470. Preferred sub-regions include one or more of: 445–459, 461–470.

Specific preferred positions contemplated include one or more of:

445,446,447,448,449,450,451,452,453,454,455,456,457, 458,459,461, 462,463,464,465,466,467,467,468,469, 470.

Specific mutations include one or more of: G447S, G456C/ P, S465P.

Preferred combinations of mutations include one or more of:

G447S+S119P,

S465P+E408R+A425T+T494A.

Increased Specific Activity

In a third aspect the invention relates to a variant of a parent glucoamylase with increased specific activity comprising one or more mutation(s) in the following position(s) or region(s) in the amino acid sequence shown in NO: 2:

Region: 1–18,

Region: 40–62,

Region: 93–127,

Region: 170–184,

Region: 200–212,

Region: 234–246,

Region: 287–319,

Region: 388–414, and/or in a corresponding position or region in a homologous glucoamylase which displays at least 60% homology with the amino acid sequences shown in SEQ ID NO: 2, with the exception of the following substitutions: S411G.

In an embodiment the region mutated is the Region: 1–18. Specific preferred positions contemplated include one or more of:

1,2,3,4,5,6,7,8,9,10,11,12,13,14,15,16,17,18,19.

Specific mutations are: L3N, I18V.

Preferred combinations of mutations include one or more of:

I18V+T51S+S56A+V59T+L60A.

In an embodiment the region mutated is the Region: 40–62. Preferred sub-regions include one or more of: 40–47, 58–62.

Specific preferred positions contemplated include one or more of: 40,41,42,43,44,45,46,47,49,51,53,56,58,59,60,61, 62.

Specific mutations include one or more of:

S40C,T43R,T51S/D,T53D,S56A/C,V59T,L60A.

Preferred combinations of mutations include one or more of:

T51S+S56A+V59T+L60A+I18V.

In an embodiment the region mutated is the Region: 93–127. In an additional embodiment the sub-region is: Region: 93–124.

Preferred sub-regions include one or more of: 93–107, 109–111, 113–115.

Specific preferred positions contemplated include one or more of:

93,94,95,96,97,98,99,100,101,102,103,104,105,106,109, 110,111,113, 114,115,117,118,126,127.

Specific mutations include one or more of: N93T, 294V, S95N, D97S, L98S/P, S100T/D, A102S/*, N110T, V111P, D112N, E113M/A, T114S, A115Q/G, Y116F, S119A, G127A.

Preferred combinations of mutations include one or more of:

S119P+Y402F,

S119P+Y402F+I189T+Y223F+F227Y.

In an embodiment the region mutated is the Region: 170–184.

Specific mutations include one or more of:

N171R/K/Q/E/W/F/Y,

Q172A/R/N/D/C/E/G/H/I/L/K/F/M/P/S/T/W/Y/V,

T173K/R/S/N/Q,

G174A,S,

Y175N/Q/D/E,

D176L

L177I

E180N/M

V181I/T

N182R/C/E/G/H/I/L/K/M/P/T/W/Y/V, preferred is E,

G183A

S184D/N/E/Q/L/I/T/R/K.

In an embodiment the region mutated is the Region: 200–212. Preferred sub-regions include: 200–211.

Specific preferred positions contemplated include one or more of:

200,201,202,203,204,205,206,207,208,209,210,211.

Specific mutations include one or more of: A201D, F202L, A203L, T204K, A205R/S, V206L/N, G207N, S208H/T/D, S209T, W212N/A/T.

In an embodiment the region mutated is the Region: 234–246. Preferred sub-regions include one or more of: 234–240, 242–245.

Specific preferred positions contemplated include one or more of:

234,235,236,237,238,239,240,242,243,244,245.

In an embodiment the region mutated is the Region: 287–319. Preferred sub-regions include one or more of: 287–292, 294–301, 313–316.

Specific preferred positions contemplated include one or more of:

287,288,289,290,291,292,294,295,296,297,298,299,300, 301,302, 303,307,308,310,311,313,314,315,316,318, 319.

Specific mutations include one or more of:

S287A/R/N/D/C/Q/E/G/H/I/L/K/M/T/V,

I288L/N/Q,

Y289F,

T290A/R/N/D/C/Q/E/G/H/I/L/K/M/P/S/V,

L291I/D/N,

N292D,

D293A/R/N/C/Q/E/G/H/I/L/K/M/S/T/V,

G294A/R/N/D/C/Q/E/G/H/I/L/K/M/P/S/T/V,

L295A/R/N/D/C/Q/E/G/H/K/M/S/T/V,

S296A/R/N/D/C/Q/E/G/H/I/L/K/M/T/V,

D297A/R/N/C/Q/E/G/H/I/L/K/M/P/S/T/V,

S298A/R/N/D/C/Q/E/G/H/I/L/K/F/M/T/V,

E299A/R/N/D/C/Q/G/H/I/L/K/M/S/T/V.

V301T/I,

A302R/N/D/C/Q/E/G/H/I/L/K/F/M/P/S/T/W/Y/V/, preferred S,

V303T/I,

G304A,

R305A/N/D/C/Q/E/G/H/I/L/F/M/P/S/T/W/Y/V,

Y306A/R/N/D/C/Q/E/G/H/I/L/K/M/P/S/T/W/V.

E308A/R/N/D/C/Q/G/H/I/L/K/M/P/S/T/V, preferred Q,

D309L,

T310V/S,

Y311N,

Y312Q/N, preferred is Q,

N313T/S/G, preferred is S,

N315Q/E/R.

In an embodiment the region mutated is the Region: 388–414. Preferred sub-regions include one or more of: 397–399,402–406, 412–414.

Specific preferred positions contemplated include one or more of:

388,389,390,394, 397,398,399,402,403,404,405,406,409, 412,413,414.

Specific mutations include one or more of: M398L, S399C/Q/T, Y402F, D403S, S405T, E408C/R, S411V, A412C, D414A.

Preferred combinations of mutations include one or more of:

Y402F+S119P,

Y402F+S119P+I189T+Y223F+F227Y.

In a preferred embodiment of the invention the regions to be mutated are:

Region: 287–300,

Region: 305–319, and/or corresponding positions or regions in a homologous glucoamylase which displays at least 60% homology with the amino acid sequences shown in SEQ ID NO: 2.

Homology (identity)

The homology referred to above of the parent glucoamylase is determined as the degree of identity between two protein sequences indicating a derivation of the first sequence from the second. The homology may suitably be determined by means of computer programs known in the art such as GAP provided in the GCG program package (Program Manual for the Wisconsin Package, Version 8, August 1994, Genetics Computer Group, 575 Science Drive, Madison, Wis., USA 53711) (Needleman, S. B. and Wunsch, C. D., (1970), Journal of Molecular Biology, 48, p. 443–453). Using Gap with the following settings for polypeptide sequence comparison: Gap creation penalty of 3.0 and Gap extension penalty of 0.1, the mature part of a polypeptide encoded by an analogous DNA sequence of the invention exhibits a degree of identity preferably of at least 60%, such as 70%, at least 80%, at least 90%, more preferably at least 95%, more preferably at least 97%, and most preferably at least 99% with the mature part of the amino acid sequence shown in SEQ ID NO: 2.

Preferably, the parent glucoamylase comprise the amino acid sequences of SEQ ID NO: 2; or allelic variants thereof; or fragments thereof that has glucoamylase activity.

A fragment of SEQ ID NO: 2 is a polypeptide which have one or more amino acids deleted from the amino and/or carboxyl terminus of this amino acid sequence. For instance, the AMG G2 (SEQ ID NO: 2) is a fragment of the Aspergillus niger G1 glucoamylase (Boel et al. (1984), EMBO J. 3 (5), p. 1097–1102) having glucoamylase activity. An allelic variant denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

The amino acid sequences of homologous parent glucoamylases may differ from the amino acid sequence of SEQ ID NO: 2 by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20–25 residues; or a small extension that facilitates purification by changing net charge or another function, such as a poly-histidine tract, an antigenic epitope or a binding domain.

In another embodiment, the isolated parent glucoamylase is encoded by a nucleic acid sequence which hybridises under very low stringency conditions, preferably low stringency conditions, more preferably medium stringency conditions, more preferably medium-high stringency conditions, even more preferably high stringency conditions, and most preferably very high stringency conditions with a nucleic acid probe which hybridises under the same conditions with (i) the nucleic acid sequence of SEQ ID NO:1, (ii) the cDNA sequence of SEQ ID NO:1, (iii) a sub-sequence of (i) or (ii), or (iv) a complementary strand of (i), (ii), or (iii) (J. Sambrook, E. F. Fritsch, and T. Maniatus, 1989, Molecular Cloning, A Laboratory Manual, 2d edition, Cold Spring Harbor, N.Y.). The sub-sequence of SEQ ID NO: 1 may be at least 100 nucleotides or preferably at least 200 nucleotides. Moreover, the sub-sequence may encode a polypeptide fragment which has glucoamylase activity. The parent polypeptides may also be allelic variants or fragments of the polypeptides that have glucoamylase activity.

The nucleic acid sequence of SEQ ID NO: 1 or a subsequence thereof, as well as the amino acid sequence of SEQ ID NO: 2, or a fragment thereof, may be used to design a nucleic acid probe to identify and clone DNA encoding polypeptides having glucoamylase activity, from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 35 nucleotides in length. Longer probes can also be used. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

Thus, a genomic DNA or cDNA library prepared from such other organisms may be screened for DNA which hybridizes with the probes described above and which encodes a polypeptide having glucoamylase. Genomic or other DNA from such other organisms may be separated by agarose or polyacrylamide gel electrophoresis, or other separation techniques. DNA from the libraries or the separated DNA may be transferred to and immobilised on nitrocellulose or other suitable carrier material. In order to identify a clone or DNA which is homologous with SEQ ID NO: 1, or sub-sequences thereof, the carrier material is used in a Southern blot. For purposes of the present invention, hybridisation indicates that the nucleic acid sequence hybridises to a nucleic acid probe corresponding to the nucleic acid sequence shown in SEQ ID NO: 1 its complementary strand, or a sub-sequence thereof, under very low to very high stringency conditions. Molecules to which the nucleic acid probe hybridises under these conditions are detected using X-ray film.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridisation, and washing post-hybridization at 5° C. to 10° C. below the calculated $T_m$ using the calculation according to Bolton and McCarthy (1962, Proceedings of the National Academy of Sciences USA 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

The present invention also relates to isolated nucleic acid sequences produced by (a) hybridising a DNA under very low, low, medium, medium-high, high, or very high stringency conditions with the sequence of SEQ ID NO:1, or its complementary strand, or a sub-sequence thereof; and (b) isolating the nucleic acid sequence. The sub-sequence is preferably a sequence of at least 100 nucleotides such as a sequence which encodes a polypeptide fragment which has glucoamylase activity.

Contemplated parent glucoamylases have at least 20%, preferably at least 40%, more preferably at least 60%, even more preferably at least 80%, even more preferably at least 90%, and most preferably at least 100% of the glucoamylase activity of the mature polypeptide of SEQ ID NO: 2.

In a preferred embodiment the variant of the invention has improved thermal stability and/or increased specific activity, preferably within the temperature interval from about 60–80° C., preferably 63–75° C., preferably at a pH of 4–5, in particular 4.2–4.7, using maltodextrin as the substrate.

In another preferred embodiment a variant of the invention is used for, e.g., alcohol fermentation.

In a preferred embodiment the parent glucoamylase is the Aspergillus niger G1 glucoamylase (Boel et al. (1984), EMBO J. 3 (5), p. 1097–1102. The parent glucoamylase may be a truncated glucoamylase, e.g., the AMG G2 glucoamylase.

Cloning a DNA Sequence Encoding A Parent Glucoamylase

The DNA sequence encoding a parent glucoamylase may be isolated from any cell or microorganism producing the glucoamylase in question, using various methods well known in the art. First, a genomic DNA and/or cDNA library should be constructed using chromosomal DNA or messenger RNA from the organism that produces the glucoamylase to be studied. Then, if the amino acid sequence of the glucoamylase is known, labeled oligonucleotide probes may be synthesized and used to identify glucoamylase-encoding clones from a genomic library prepared from the organism in question. Alternatively, a labelled oligonucleotide probe containing sequences homologous to another known glucoamylase gene could be used as a probe to identify glucoamylase-encoding clones, using hybridization and washing conditions of very low to very high stringency. This is described above.

Yet another method for identifying glucoamylase-encoding clones would involve inserting fragments of genomic DNA into an expression vector, such as a plasmid, transforming glucoamylase-negative bacteria with the resulting genomic DNA library, and then plating the transformed bacteria onto agar containing a substrate for glucoamylase (i.e., maltose), thereby allowing clones expressing the glucoamylase to be identified.

Alternatively, the DNA sequence encoding the enzyme may be prepared synthetically by established standard methods, e.g. the phosphoroamidite method described S. L. Beaucage and M. H. Caruthers, (1981), Tetrahedron Letters 22, p. 1859–1869, or the method described by Matthes et al., (1984), EMBO J. 3, p. 801–805. In the phosphoroamidite method, oligonucleotides are synthesized, e.g., in an automatic DNA synthesizer, purified, annealed, ligated and cloned in appropriate vectors.

Finally, the DNA sequence may be of mixed genomic and synthetic origin, mixed synthetic and cDNA origin or mixed genomic and cDNA origin, prepared by ligating fragments of synthetic, genomic or cDNA origin (as appropriate, the fragments corresponding to various parts of the entire DNA sequence), in accordance with standard techniques. The DNA sequence may also be prepared by polymerase chain reaction (PCR) using specific primers, for instance as described in U.S. Pat. No. 4,683,202 or R. K. Saiki et al., (1988), Science 239, 1988, pp. 487–491.

Site-directed Mutagenesis

Once a glucoamylase-encoding DNA sequence has been isolated, and desirable sites for mutation identified, mutations may be introduced using synthetic oligonucleotides. These oligonucleotides contain nucleotide sequences flanking the desired mutation sites. In a specific method, a single-stranded gap of DNA, the glucoamylase-encoding sequence, is created in a vector carrying the glucoamylase gene. Then the synthetic nucleotide, bearing the desired mutation, is annealed to a homologous portion of the single-stranded DNA. The remaining gap is then filled in with DNA polymerase I (Klenow fragment) and the construct is ligated using T4 ligase. A specific example of this method is described in Morinaga et al., (1984), Biotechnology 2, p. 646–639. U.S. Pat. No. 4,760,025 discloses the introduction of oligonucleotides encoding multiple mutations by performing minor alterations of the cassette. However, an even greater variety of mutations can be introduced at any one time by the Morinaga method, because a multitude of oligonucleotides, of various lengths, can be introduced.

Another method for introducing mutations into glucoamylase-encoding DNA sequences is described in Nelson and Long, (1989), Analytical Biochemistry 180, p. 147–151. It involves the 3-step generation of a PCR fragment containing the desired mutation introduced by using a chemically synthesized DNA strand as one of the primers in the PCR reactions. From the PCR-generated fragment, a DNA fragment carrying the mutation may be isolated by cleavage with restriction endonucleases and reinserted into an expression plasmid.

Further, Sierks. et al., (1989), Protein Eng., 2, 621–625; Sierks et al., (1990), Protein Eng. vol. 3, 193–198; also describes site-directed mutagenesis in an Aspergillus glucoamylase.

Random Mutagenesis

Random mutagenesis is suitably performed either as localized or region-specific random mutagenesis in at least three parts of the gene translating to the amino acid sequence shown in question, or within the whole gene.

The random mutagenesis of a DNA sequence encoding a parent glucoamylase may be conveniently performed by use of any method known in the art.

In relation to the above, a further aspect of the present invention relates to a method for generating a variant of a parent glucoamylase, wherein the variant exhibits increased thermal stability relative to the parent, the method comprising:

(a) subjecting a DNA sequence encoding the parent glucoamylase to random mutagenesis, (b) expressing the mutated DNA sequence obtained in step (a) in a host cell, and (c) screening for host cells expressing a glucoamylase variant which has an altered property (i.e. thermal stability) relative to the parent glucoamylase.

Step (a) of the above method of the invention is preferably performed using doped primers, as described in the working examples herein (vide infra).

For instance, the random mutagenesis may be performed by use of a suitable physical or chemical mutagenizing agent, by use of a suitable oligonucleotide, or by subjecting the DNA sequence to PCR generated mutagenesis. Furthermore, the random mutagenesis may be performed by use of any combination of these mutagenizing agents. The mutagenizing agent may, e.g., be one which induces transitions, transversions, inversions, scrambling, deletions, and/or insertions.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues. When such agents are used, the mutagenesis is typically performed by incubating the DNA sequence encoding the parent enzyme to be mutagenized in the presence of the mutagenizing agent of choice under suitable conditions for the mutagenesis to take place, and selecting for mutated DNA having the desired properties.

When the mutagenesis is performed by the use of an oligonucleotide, the oligonucleotide may be doped or spiked with the three non-parent nucleotides during the synthesis of the oligonucleotide at the positions which are to be changed. The doping or spiking may be done so that codons for unwanted amino acids are avoided. The doped or spiked oligonucleotide can be incorporated into the DNA encoding the glucoamylase enzyme by any published technique, using, e.g., PCR, LCR or any DNA polymerase and ligase as deemed appropriate.

Preferably, the doping is carried out using "constant random doping", in which the percentage of wild-type and mutation in each position is predefined. Furthermore, the doping may be directed toward a preference for the introduction of certain nucleotides, and thereby a preference for the introduction of one or more specific amino acid residues. The doping may be made, e.g., so as to allow for the introduction of 90% wild type and 10% mutations in each position. An additional consideration in the choice of a doping scheme is based on genetic as well as protein-structural constraints. The doping scheme may be made by using the DOPE program which, inter alia, ensures that introduction of stop codons is avoided.

When PCR-generated mutagenesis is used, either a chemically treated or non-treated gene encoding a parent glucoamylase is subjected to PCR under conditions that increase the mis-incorporation of nucleotides (Deshler 1992; Leung et al., Technique, Vol.1, 1989, pp. 11–15).

A mutator strain of *E. coli* (Fowler et al., Molec. Gen. Genet., 133, 1974, pp. 179–191), *S. cereviseae* or any other microbial organism may be used for the random mutagenesis of the DNA encoding the glucoamylase by, e.g., transforming a plasmid containing the parent glycosylase into the mutator strain, growing the mutator strain with the plasmid and isolating the mutated plasmid from the mutator strain. The mu-ta-ted plasmid may be subsequently transformed into the expression organism.

The DNA sequence to be mutagenized may be conveniently present in a genomic or cDNA library prepared from an organism expressing the parent glucoamylase. Alternatively, the DNA sequence may be present on a suitable vector such as a plasmid or a bacteriophage, which as such may be incubated with or otherwise exposed to the mutagenising agent. The DNA to be mutagenized may also be present in a host cell either by being integrated in the genome of said cell or by being present on a vector harboured in the cell. Finally, the DNA to be mutagenized may be in isolated form. It will be understood that the DNA sequence to be subjected to random mutagenesis is preferably a cDNA or a genomic DNA sequence.

In some cases it may be convenient to amplify the mutated DNA sequence prior to performing the expression step b) or the screening step c). Such amplification may be performed in accordance with methods known in the art, the presently preferred method being PCR-generated amplification using oligonucleotide primers prepared on the basis of the DNA or amino acid sequence of the parent enzyme.

Subsequent to the incubation with or exposure to the mutagenising agent, the mutated DNA is expressed by culturing a suitable host cell carrying the DNA sequence under conditions allowing expression to take place. The host cell used for this purpose may be one which has been transformed with the mutated DNA sequence, optionally present on a vector, or one which carried the DNA sequence encoding the parent enzyme during the mutagenesis treatment. Examples of suitable host cells are the following: gram positive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis, Streptomyces lividans* or *Streptomyces murinus*; and gram-negative bacteria such as *E. coli*.

The mutated DNA sequence may further comprise a DNA sequence encoding functions permitting expression of the mutated DNA sequence.

Localized Random Mutagenesis

The random mutagenesis may be advantageously localized to a part of the parent glucoamylase in question. This may, e.g., be advantageous when certain regions of the enzyme have been identified to be of particular importance for a given property of the enzyme, and when modified are expected to result in a variant having improved properties. Such regions may normally be identified when the tertiary structure of the parent enzyme has been elucidated and related to the function of the enzyme.

The localized, or region-specific, random mutagenesis is conveniently performed by use of PCR generated mutagenesis techniques as described above or any other suitable technique known in the art. Alternatively, the DNA sequence encoding the part of the DNA sequence to be modified may be isolated, e.g., by insertion into a suitable vector, and said part may be subsequently subjected to mutagenesis by use of any of the mutagenesis methods discussed above.

Alternative methods for providing variants of the invention include gene shuffling e.g. as described in WO 95/22625 (from Affymax Technologies N.V.) or in WO 96/00343 (from Novo Nordisk A/S).

Expression Of Glucoamylase Variants

According to the invention, a DNA sequence encoding the variant produced by methods described above, or by any alternative methods known in the art, can be expressed, in enzyme form, using an expression vector which typically includes control sequences encoding a promoter, operator, ribosome binding site, translation initiation signal, and, optionally, a repressor gene or various activator genes.

Expression Vector

The recombinant expression vector carrying the DNA sequence encoding a glucoamylase variant of the invention may be any vector which may conveniently be subjected to recombinant DNA procedures, and the choice of vector will often depend on the host cell into which it is to be introduced. The vector may be one which, when introduced into a host cell, is integrated into the host cell genome and replicated together with the chromosome(s) into which it has been integrated. Examples of suitable expression vectors include pMT838.

Promoter

In the vector, the DNA sequence should be operably connected to a suitable promoter sequence. The promoter may be any DNA sequence which shows transcriptional activity in the host cell of choice and may be derived from genes encoding proteins either homologous or heterologous to the host cell.

Examples of suitable promoters for directing the transcription of the DNA sequence encoding a glucoamylase variant of the invention, especially in a bacterial host, are the promoter of the lac operon of *E.coli*, the *Streptomyces coelicolor* agarase gene dagA promoters, the promoters of the *Bacillus licheniformis* α-amylase gene (amyL), the promoters of the *Bacillus stearothermophilus* maltogenic amylase gene (amyM), the promoters of the *Bacillus amyloliquefaciens* α-amylase (amyQ), the promoters of the *Bacillus subtilis* xylA and xylB genes etc. For transcription in a fungal host, examples of useful promoters are those derived from the gene encoding *A. oryzae* TAKA amylase, the TPI (triose phosphate isomerase) promoter from *S. cerevisiae* (Alber et al. (1982), J. Mol. Appl. Genet 1, p. 419–434, *Rhizomucor miehei* aspartic proteinase, *A. niger* neutral α-amylase, *A. niger* acid stable α-amylase, *A. niger* glucoamylase, *Rhizomucor miehei* lipase, *A. oryzae* alkaline protease, *A. oryzae* triose phosphate isomerase or *A. nidulans* acetamidase.

Expression Vector

The expression vector of the invention may also comprise a suitable transcription terminator and, in eukaryotes, polyadenylation sequences operably connected to the DNA sequence encoding the α-amylase variant of the invention. Termination and polyadenylation sequences may suitably be derived from the same sources as the promoter.

The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e.g. a gene the product of which complements a defect in the host cell, such as the dal genes from *B. subtilis* or *B. licheniformis*, or one which confers antibiotic resistance such as ampicillin, kanamycin, chloramphenicol or tetracyclin resistance. Furthermore, the vector may comprise Aspergillus selection markers such as amdS, argB, niaD and sC, a marker giving rise to hygromycin resistance, or the selection may be accomplished by co-transformation, e.g. as described in WO 91/17243.

The procedures used to ligate the DNA construct of the invention encoding a glucoamylase variant, the promoter, terminator and other elements, respectively, and to insert them into suitable vectors containing the information necessary for replication, are well known to persons skilled in the art (cf., for instance, Sambrook et al., *Molecular Cloning: A Laboratory Manual*, 2nd Ed., Cold Spring Harbor, 1989).

Host Cells

The cell of the invention, either comprising a DNA construct or an expression vector of the invention as defined above, is advantageously used as a host cell in the recombinant production of a glucoamylase variant of the invention. The cell may be transformed with the DNA construct of the invention encoding the variant, conveniently by integrating the DNA construct (in one or more copies) in the host chromosome. This integration is generally considered to be an advantage as the DNA sequence is more likely to be stably maintained in the cell. Integration of the DNA constructs into the host chromosome may be performed according to conventional methods, e.g. by homologous or heterologous recombination. Alternatively, the cell may be transformed with an expression vector as described above in connection with the different types of host cells.

The cell of the invention may be a cell of a higher organism such as a mammal or an insect, but is preferably a microbial cell, e.g., a bacterial or a fungal (including yeast) cell.

Examples of suitable bacteria are Gram positive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis*, or *Streptomyces lividans* or *Streptomyces murinus*, or gramnegative bacteria such as *E.coli*. The transformation of the bacteria may, for instance, be effected by protoplast transformation or by using competent cells in a manner known per se.

The yeast organism may favorably be selected from a species of Saccharomyces or Schizosaccharomyces, e.g. *Saccharomyces cerevisiae*.

The host cell may also be a filamentous fungus e.g. a strain belonging to a species of Aspergillus, most preferably *Aspergillus oryzae* or *Aspergillus niger*, or a strain of Fusarium, such as a strain of *Fusarium oxysporium, Fusarium graminearum* (in the perfect state named *Gribberella zeae*, previously *Sphaeria zeae*, synonym with *Gibberella roseum* and *Gibberalla roseum* f. sp. cerealis), or *Fusarium sulphureum* (in the prefect state named *Gibberella puricaris*, synonym with *Fusarium trichothecioides, Fusarium bactridioides, Fusarium sambucium, Fusariurn roseum*, and *Fusarium roseum* var. *gramioearum*), *Fusarium cerealis* (synonym with *Fusariurn crokkwellnse*), or *Fusarium venenatum*.

In a preferred embodiment of the invention the host cell is a protease deficient or protease minus strain.

This may for instance be the protease deficient strain *Aspergillus oryzae* JaL 125 having the alkaline protease gene named "alp" deleted. This strain is described in WO 97/35956 (Novo Nordisk).

Filamentous fungi cells may be transformed by a process involving protoplast formation and transformation of the protoplasts followed by regeneration of the cell wall in a manner known per se. The use of Aspergillus as a host micro-organism is described in EP 238 023 (Novo Nordisk A/S), the contents of which are hereby incorporated by reference.

Method Of Producing A Glucoamylase Variant

In a yet further aspect, the present invention relates to a method of producing a glucoamylase variant of the invention, which method comprises cultivating a host cell under conditions conducive to the production of the variant and recovering the variant from the cells and/or culture medium.

The medium used to cultivate the cells may be any conventional medium suitable for growing the host cell in question and obtaining expression of the glucoamylase variant of the invention. Suitable media are available from commercial suppliers or may be prepared according to published recipes (e.g. as described in catalogues of the American Type Culture Collection).

The glucoamylase variant secreted from the host cells may conveniently be recovered from the culture medium by well-known procedures, including separating the cells from the medium by centrifugation or filtration, and precipitating proteinaceous components of the medium by means of a salt such as ammonium sulphate, followed by the use of chromatographic procedures such as ion exchange chromatography, affinity chromatography, or the like.

Starch Conversion

The present invention provides a method of using glucoamylase variants of the invention for producing glucose and the like from starch. Generally, the method includes the steps of partially hydrolyzing precursor starch in the presence of α-amylase and then further hydrolyzing the release of D-glucose from the non-reducing ends of the starch or related oligo- and polysaccharide molecules in the presence of glucoamylase by cleaving α-(1→4) and α-(1→6) glucosidic bonds.

The partial hydrolysis of the precursor starch utilizing α-amylase provides an initial breakdown of the starch molecules by hydrolyzing internal α-(1→4)-linkages. In commercial applications, the initial hydrolysis using α-amylase is run at a temperature of approximately 105° C.

A very high starch concentration is processed, usually 30% to 40% solids. The initial hydrolysis is usually carried out for five minutes at this elevated temperature. The partially hydrolyzed starch can then be transferred to a second tank and incubated for approximately 1–2 hour at a temperature of 85° to 98° C. to derive a dextrose equivalent (D.E.) of 10 to 15.

The step of further hydrolyzing the release of D-glucose from the non-reducing ends of the starch or related oligo- and polysaccharides molecules in the presence of glucoamylase is normally carried out in a separate tank at a reduced temperature between 30° and 62° C. Preferably the temperature of the substrate liquid is dropped to between 55° and 60° C. The pH of the solution is dropped from about 5.5 to 6.5 to a range between 3 and 5.5. Preferably, the pH of the solution is 4 to 4.5. The glucoamylase is added to the solution and the reaction is carried out for 24–72 hours, preferably 36–48 hours.

By using a thermostable glucoamylase variant of the invention saccharification processes may be carried out at a higher temperature than traditional batch saccharification processes. According to the invention saccharification may be carried out at temperatures in the range from above 60–80° C., preferably 63–75° C. This apply both for traditional batch processes (described above) and for continuous saccharification processes.

Actually, continuous saccharification processes including one or more membrane separation steps, i.e. filtration steps, must be carried out at temperatures of above 60° C. to be able to maintain a reasonably high flux over the membrane or to minimize microbial contamination. Therefore, the thermostable variants of the invention provides the possibility of carrying out large scale continuous saccharification processes at a fair price and/or at a lower enzyme protein dosage within a period of time acceptable for industrial saccharification processes. According to the invention the saccharification time may even be shortened.

The activity of the glucoamylase variant (e.g. AMG variant) of the invention is generally substantially higher at temperatures between 60° C.–80° C. than at the traditionally used temperature between 30–60° C. Therefore, by increasing the temperature at which the glucoamylase operates the saccharification process may be carried out within a shorter period of time.

Further, by improving the thermal stability the $T_{1/2}$ (half-time, as defined in the "Materials and Methods" section) is improved. As the thermal stability of the glucoamylase variants of the invention is improved a minor amount of glucoamylase need to be added to replace the glucoamylase being inactivated during the saccharification process. More glucoamylase is maintained active during saccharification process according to the present invention. Furthermore, the risk of microbial contamination is also reduced when carrying the saccharification process at temperature above 63° C.

The glucose yield from a typical saccharification trial with glucoamylase, acid amylase and pullulanase is 95.5–96.5%. The remaining carbohydrates typically consists of 1% maltose, 1.5–2% isomaltose and 1–1.5% higher oligosaccharides. The disaccharides are produced since the glucoamylase at high concentrations of glucose and high dry-solid levels has a tendency to form reversion products.

A glucoamylase with an increased specific activity towards saccharides present in the solution after liquefaction and saccharides formed during saccharification would be an advantage as a reduced enzyme protein dosage or a shorter process time then could be used. In general, the glucoamylase has a preference for substrates consisting of longer saccharides compared to short chain saccharides and the specific activity towards e.g. maltoheptaose is therefore approximately 6 times higher than towards maltose. An increased specific activity towards short chain saccharides such as maltose (without reducing the activity towards oligosaccharides) would therefore also permit using a lower enzyme dosage and/or shorter process time.

Furthermore, a higher glucose yield can be obtained with a glucoamylase variant with an increased alpha-1,4 hydrolytic activity (if the alpha-1,6 activity is unchanged or even decreased), since a reduced amount of enzyme protein is being used, and alpha-1,6 reversion product formation therefore is decreased (less isomaltose).

The specific activity may be measured using the method described in the "Materials & Methods" section at 37° C. or 60° C.

Example of saccharification process wherein the glucoamylase variants of the invention may be used include the processes described in JP 3-224493; JP 1-191693;JP 62-272987; EP 452,238, and WO 99/27124 (all references are hereby incorporated by reference).

In a further aspect the invention relates to a method of saccharifying a liquefied starch solution, comprising the steps (i) a saccharification step during which step one or more enzymatic saccharification stages takes place, and the subsequent step of (ii) one or more high temperature membrane separation steps wherein the enzymatic saccharification is carried out using a thermostable glucoamylase variant of the invention.

The glucoamylase variant(s) of the invention may be used in the present inventive process in combination with an enzyme that hydrolyzes only α-(1→6)-glucosidic bonds in molecules with at least four glucosyl residues. Preferentially, the glucoamylase variant of the invention can be used in combination with pullulanase or isoamylase. The use of isoamylase and pullulanase for debranching, the molecular properties of the enzymes, and the potential use of the enzymes with glucoamylase is set forth in G.M.A. van Beynum et al., Starch Conversion Technology, Marcel Dekker, New York, 1985, 101–142.

In a further aspect the invention relates to the use of a glucoamylase variant of the invention in a starch conversion process.

Further, the glucoamylase variant of the invention may be used in a continuous starch conversion process including a continuous saccharification step.

The glucoamylase variants of the invention may also be used in immobilised form. This is suitable and often used for producing speciality syrups, such as maltose syrups, and further for the raffinate stream of oligosaccharides in connection with the production of fructose syrups.

The glucoamylase of the invention may also be used in a process for producing ethanol for fuel or beverage or may be used in a fermentation process for producing organic compounds, such as citric acid, ascorbic acid, lysine, glutamic acid.

MATERIALS & METHODS

MATERIALS

Enzymes

AMG G1: *Aspergillus niger* glucoamylase G1 disclosed in Boel et al. (1984), EMBO J. 3 (5), 1097–1102, and SEQ ID NO: 13, available from Novo Nordisk.

AMG G2: Truncated *Aspergillus niger* glucoamylase G1 shown in SEQ ID NO: 2, available from Novo Nordisk)

Solutions

Buffer: 0.05M sodium acetate (6.8 g in 1 milli-Q-water), pH 4.5

Stop solution: 0.4M NaOH

GOD-perid, 124036, Boehringer Mannheim

Substrate

Maltose: 29 mM (1 g maltose in 100 ml 50 mM sodium acetate, pH 4.5) (Sigma)

Maltoheptaose: 10 mM, 115 mg/10 ml (Sigma)

Host Cell

*A. oryzae* JaL 125: *Aspergillus oryzae* IFO 4177 available from Institute for Fermention, Osaka; 17–25 Juso Hammachi 2-Chome Yodogawa-ku, Osaka, Japan, having the alkaline protease gene named "alp" (described by Murakami K et al., (1991), Agric. Biol. Chem. 55, p. 2807–2811) deleted by a one step gene replacement method (described by G. May in "Applied Molecular Genetics of Filamentous Fungi" (1992), p. 1–25. Eds. J. R. Kinghorn and G. Turner; Blackie Academic and Professional), using the *A. oryzae* pyrG gene as marker. Strain JaL 125 is further disclosed in WO 97/35956 (Novo Nordisk).

Micro-organisms

Strain: *Saccharomyces cerevisiae* YNG318: MATαleu2-Δ2 ura3-52 his4-539 pep4-Δ1[cir+]

Plasmids pCAMG91: see FIG. 1. Plasmid comprising the *Aspergillus niger* G1 glucoamylase (AMG G1). The construction of pCAMG91 is described in Boel et al. (1984), EMBO J. 3 (7) p.1581–1585.

pMT838: Plasmid encoding the truncated *Aspergillus niger* glucoamylase G2 (SEQ ID NO: 2).

pJSO026 (*S. cerevisiae* expression plasmid)(J. S. Okkels, (1996) "A URA3-promoter deletion in a pYES vector increases the expression level of a fungal lipase in *Saccharomyces cerevisiae*. Recombinant DNA Biotechnology III: The Integration of Biological and Engineering Sciences, vol. 782 of the Annals of the New York Academy of Sciences). More specifically, the expression plasmid pJSO37, is derived from pYES 2.0 by replacing the inducible GAL1 promoter of pYES 2.0 with the constitutively expressed TPI (triose phosphate isomerase)-promoter from *Saccharomyces cerevisiae* (Albert and Karwasaki, (1982), J. Mol. Appl Genet., 1, 419–434), and deleting a part of the URA3 promoter.

METHODS

Transformation of *Saccharomyces cerevisiae* YNG318

The DNA fragments and the opened vectors are mixed and transformed into the yeast *Saccharomyces cerevisiae* YNG318 by standard methods.

Determining Specific Activity As $k_{cat}$ (sec.$^{-1}$)

750 microL substrate (1% maltose, 50 mM Sodium acetat, pH 4.3) is incubated 5 minutes at selected temperature, such as 37° C. or 60° C.

50 microL enzyme diluted in sodium acetate is added.

Aliquots of 100 microL are removed after 0, 3, 6, 9 and 12 minutes and transferred to 100 microL 0.4 M Sodium hydroxide to stop the reaction. A blank is included.

20 microL is transferred to a Micro titre plates and 200 microL GOD-Perid solution is added. Absorbance is measured at 650 nm after 30 minutes incubation at room temperature.

Glucose is used as standard and the specific activity is calculated as $k_{cat}$ (sec.$^{-1}$).

Determination Of AGU Activity and As AGU/mg

One Novo Amyloglucosidase Unit (AGU) is defined as the amount of enzyme which hydrolyzes 1 micromole maltose per minute at 37° C. and pH 4.3. A detailed description of the analytical method (AEL-SM-0131) is available on request from Novo Nordisk.

The activity is determined as AGU/ml by a method modified after (AEL-SM-0131) using the Glucose GOD-Perid kit from Boehringer Mannheim, 124036. Standard: AMG-standard, batch 7-1195, 195 AGU/ml.

375 microL substrate (1% maltose in 50 mM Sodium acetate, pH 4.3) is incubated 5 minutes at 37° C. 25 microL enzyme diluted in sodium acetate is added. The reaction is stopped after 10 minutes by adding 100 microL 0.25 M NaOH. 20 microL is transferred to a 96 well microtitre plate and 200 microL GOD-Perid solution is added. After 30 minutes at room temperature, the absorbance is measured at 650 nm and the activity calculated in AGU/ml from the AMG-standard.

The specific activity in AGU/mg is then calculated from the activity (AGU/ml) divided with the protein concentration (mg/ml).

Transformation Of *Aspergillus oryzae* (general procedure)

100 ml of YPD (Sherman et al., (1981), Methods in Yeast Genetics, Cold Spring Harbor Laboratory) are inoculated with spores of *A. oryzae* and incubated with shaking for about 24 hours. The mycelium is harvested by filtration through miracloth and washed with 200 ml of 0.6 M MgSO$_4$. The mycelium is suspended in 15 ml of 1.2 M MgSO$_4$, 10 mM NaH$_2$PO$_4$, pH 5.8. The suspension is cooled on ice and 1 ml of buffer containing 120 mg of Novozym™ 234 is added. After 5 min., 1 ml of 12 mg/ml BSA (Sigma type H25) is added and incubation with gentle agitation continued for 1.5–2.5 hours at 37° C. until a large number of protoplasts is visible in a sample inspected under the microscope.

The suspension is filtered through miracloth, the filtrate transferred to a sterile tube and overlayed with 5 ml of 0.6 M sorbitol, 100 mM Tris-HCl, pH 7.0. Centrifugation is performed for 15 min. at 1000 g and the protoplasts are collected from the top of the MgSO$_4$ cushion. 2 volumes of STC (1.2 M sorbitol, 10 mM Tris-HCl, pH 7.5, 10 mM CaCl$_2$) are added to the protoplast suspension and the mixture is centrifugated for 5 min. at 1000 g. The protoplast pellet is resuspended in 3 ml of STC and repelleted. This is repeated. Finally, the protoplasts are resuspended in 0.2–1 ml of STC.

100 μl of protoplast suspension are mixed with 5–25 μg of p3SR2 (an *A. nidulans* amdS gene carrying plasmid described in Hynes et al., Mol. and Cel. Biol., Vol. 3, No. 8, 1430–1439, Aug. 1983) in 10 μl of STC. The mixture is left at room temperature for 25 min. 0.2 ml of 60% PEG 4000 (BDH 29576), 10 mM $CaCl_2$ and 10 mM Tris-HCl, pH 7.5 is added and carefully mixed (twice) and finally 0.85 ml of the same solution are added and carefully mixed. The mixture is left at room temperature for 25 min., spun at 2.500 g for 15 min. and the pellet is resuspended in 2 ml of 1.2M sorbitol. After one more sedimentation the protoplasts are spread on minimal plates (Cove, (1966), Biochem. Biophys. Acta 113, 51–56) containing 1.0 M sucrose, pH 7.0, 10 mM acetamide as nitrogen source and 20 mM CsCl to inhibit background growth. After incubation for 4–7 days at 37° C. spores are picked, suspended in sterile water and spread for single colonies. This procedure is repeated and spores of a single colony after the second re-isolation are stored as a defined transformant.

Fed Batch Fermentation

Fed batch fermentation is performed in a medium comprising maltodextrin as a carbon source, urea as a nitrogen source and yeast extract. The fed batch fermentation is performed by inoculating a shake flask culture of *A. oryzae* host cells in question into a medium comprising 3.5% of the carbon source and 0.5% of the nitrogen source. After 24 hours of cultivation at pH 5.0 and 34° C. the continuous supply of additional carbon and nitrogen sources are initiated. The carbon source is kept as the limiting factor and it is secured that oxygen is present in excess. The fed batch cultivation is continued for 4 days, after which the enzymes can be recovered by centrifugation, ultrafiltration, clear filtration and germ filtration.

Purification

The culture broth is filtrated and added ammoniumsulphate (AMS) to a concentration of 1.7 M AMS and pH is adjusted to pH 5. Precipitated material is removed by centrifugation and the solution containing glucoamylase activity is applied on a Toyo Pearl Butyl column previously equilibrated in 1.7 M AMS, 20 mM sodium acetate, pH 5. Unbound material is washed out with the equilibration buffer. Bound proteins are eluted with 10 mM sodium acetate, pH 4.5 using a linear gradient from 1.7–0 M AMS over 10 column volumes. Glucoamylase containing fractions are collected and dialysed against 20 mM sodium acetate, pH 4.5. The solution was then applied on a Q sepharose column, previously equilibrated in 10 mM Piperazin, Sigma, pH 5.5. Unbound material is washed out with the equilibration buffer. Bound proteins are eluted with a linear gradient of 0–0.3 M Sodium chloride in 10 mM Piperazin, pH 5.5 over 10 column volumes. Glucoamylase containing fractions are collected and the purity was confirmed by SDS-PAGE.

$T_{1/2}$ (half-life) Method I

The thermal stability of variants is determined as $T_{1/2}$ using the following method: 950 microliter 50 mM sodium acetate buffer (pH 4.3) (NaOAc) is incubated for 5 minutes at 68° C. or 70° C. 50 microliter enzyme in buffer (4 AGU/ml) is added. 2×40 microliter samples are taken at 0, 5, 10, 20, 30 and 40 minutes and chilled on ice. The activity (AGU/ml) measured before incubation (0 minutes) is used as reference (100%). The decline in stability (in percent) is calculated as a function of the incubation time. The % residual glucoamylase activity is determined at different times. $T_{1/2}$ is the period of time until which the % relative activity is decreased to 50%. $T_{T½}$ (half-life) (Method II) The $T_{1/2}$ is measured by incubating the enzyme (ca 0.2 AGU/ml) in question in 30% glucose, 50 mM Sodium acetate at pH 4.5 at the temperature in question (e.g., 70° C.). Samples are withdrawn at set time intervals and chilled on ice and residual enzyme activity measured by the pNPG method (as described below).

The % residual glucoamylase activity is determined at different times. $T_{1/2}$ is the period of time until which the % relative activity is decreased to 50%.

Residual Enzyme Activity (pNPG method)

pNPG reagent:

0.2 g pNPG (p-nitrophenylglucopyranoside) is dissolved in 0.1 M acetate buffer (pH 4.3) and made up to 100 ml.

Borate solution:

3.8 g $Na_2B_4O_7.10\ H_2O$ is dissolved in Milli-Q water and made up to 100 ml.

25 microL samples are added 50 microL substrate and incubated 2 hr at 50° C. The reaction is stopped by adding 150 micoL ml borate solution. The optical density is measured at 405 nm, and the residual activity calculated.

Construction Of pAMGY

The pAMGY vector was constructed as follows: The lipase gene in pJSO026 was replaced by the AMG gene, which was PCR amplified with the forward primer; FG2: 5'-CAT CCC CAG GAT CCT TAC TCA GCA ATG-3' and the reverse primer: RG2: 5'-CTC AAA CGA CTC ACC AGC CTC TAG AGT-3' using the template plasmid pLAC103 containing the AMG gene. The pJSO026 plasmid was digested with XbaI and SmaI at 37° C. for 2 hours and the PCR amplicon was blunt ended using the Klenow fragment and then digested with XbaI. The vector fragment and the PCR amplicon were ligated and transformed into *E. coli* by electrotransformation. The resulting vector is designated pAMGY.

Construction Of pLaC103

The *A. niger* AMGII cDNA clone (Boel et al., (1984), supra) is used as source for the construction of pLaC103 aimed at *S. cerevisiae* expression of the GII form of AMG.

The construction takes place in several steps, out lined below.

pT7–212 (EP37856/U.S. Pat. No. 5,162,498) is cleaved with XbaI, blunt-ended with Klenow DNA polymerase and dNTP. After cleavage with EcoRI the resulting vector fragment is purified from an agarose gel-electrophoresis and ligated with the 2.05 kb EcoRl-EcoRV fragment of pBoel53, thereby recreating the XbaI site in the EcoRV end of the AMG encoding fragment in the resulting plasmid pG2x.

In order to remove DNA upstream of the AMG cds, and furnish the AMG encoding DNA with an appropriate restriction endonuclease recognition site, the following construct was made:

The 930 bp EcoRI-PstI fragment of p53 was isolated and subjected to AluI cleavage, the resulting 771 bp Alu-PstI fragment was ligated into pBR322 with blunt-ended EcoRI site (see above) and cleaved with PstI In the resulting plasmid pBR-AMG', the EcoRI site was recreated just 34 bp from the initiation codon of the AMG cds.

From pBR-AMG' the 775 bp EcoRI-PstI fragment was isolated and joined with the 1151 bp PstI-XbaI fragment from pG2x in a ligation reaction including the XbaI-EcoRI vector fragment of pT7-212.

The resulting plasmid pT7GII was submitted to a BamHI cleavage in presence of alkaline phosphatase followed by partial SphI cleavage after inactivation of the phosphatase. From this reaction was the 2489 bp SphI-BamHI fragment, encompassing the S.c. TPI promoter linked to the AMGII cds. The above fragment together with the 1052 bp BamHI fragment of pT7GII was ligated with the alkaline phosphatase treated vector fragment of pMT743 (EP37856/U.S. Pat. No. 5,162,498), resulting from SphI-BamHI digestion. The resulting plasmid is pLaC103.

Screening For Thermostable AMG Variants

The libraries are screened in the thermostable filter assay described below.

Filter Assay For Thermostability

Yeast libraries are plated on a sandwich of cellulose acetate (OE 67, Schleicher & Schuell, Dassel, Germany)— and nitrocellulose filters (Protran-Ba 85, Schleicher & Schuell, Dassel, Germany) on SCFura¯agar plates with 100 µg/ml ampicillin at 30° C. for at least 72 hrs. The colonies are replica plated to PVDF filters (Immobilon-P, Millipore, Bedford) activated with methanol for 1 min or alternatively a Protran filter (no activation) and subsequently washed in 0.1 M NaAc and then incubated at room temperature for 2 hours. Colonies are washed from PVDF/Protran filters with tap water. Each filter sandwiches and PVDF/Protran filters are specifically marked with a needle before incubation in order to be able to localise positive variants on the filters after the screening. The PVDF filters with bound variants are transferred to a container with 0.1 M NaAC, pH 4.5 and incubated at 47° C. or alternatively 67–69° C. in case of Protran filters for 15 minutes. The sandwich of cellulose acetate and nitrocellulose filters on SC ura-agar plates are stored at room temperature until use. After incubation, the residual activities are detected on plates containing 5% maltose, 1% agarose, 50 mM NaAc, pH 4.5. The assay plates with PVDF filters are marked the same way as the filter sandwiches and incubated for 2 hrs. at 50° C. After removal of the PVDF filters, the assay plates are stained with Glucose GOD perid (Boehringer Mannheim GmbH, Germany). Variants with residual activity are detected on assay plates as dark green spots on white background. The improved variants are located on the storage plates. Improved variants are rescreened twice under the same conditions as the first screen.

General Method For Random Mutagenesis By Use Of The DOPE Program

The random mutagenesis may be carried out by the following steps:
1. Select regions of interest for modification in the parent enzyme,
2. Decide on mutation sites and non-mutated sites in the selected region,
3. Decide on which kind of mutations should be carried out, e.g., with respect to the desired stability and/or performance of the variant to be constructed,
4. Select structurally reasonable mutations,
5. Adjust the residues selected by step 3 with regard to step 4.
6. Analyze by use of a suitable dope algorithm the nucleotide distribution.
7. If necessary, adjust the wanted residues to genetic code realism, e.g. taking into account constraints resulting from the genetic code, e.g. in order to avoid introduction of stop codons; the skilled person will be aware that some codon combinations cannot be used in practice and will need to be adapted
8. Make primers
9. Perform random mutagenesis by use of the primers
10. Select resulting glucoamylase variants by screening for the desired improved properties.

Dope Algorithm

Suitable dope algorithms for use in step 6 are well known in the art. One such algorithm is described by Tomandl, D. et al., 1997, Journal of Computer-Aided Molecular Design 11:29–38. Another algorithm is DOPE (Jensen, L J, Andersen, K V, Svendsen, A, and Kretzschmar, T (1998) Nucleic Acids Research 26:697–702).

Method Of Extracting Important Regions For Temperature Activity Using Molecular Simulation The X-ray structure and/or the model-build structure of the enzyme of interest, here AMG, are subjected to molecular dynamics simulations. The molecular dynamics simulation are made using the CHARMM (from Molecular simulations (MSI)) program or other suitable programs, e.g., DISCOVER (from MSI). The dynamics are made in vacuum, or including crystal waters, or with the enzyme in question embedded in a suitable waters, e.g., a sphere or a box. The simulation are run for 300 picoseconds (ps) or more, e.g., 300–1200 ps. The isotropic fluctuations are extracted for the CA carbons of the structures and comparison between the structures are made. More details on how to get the isotropic fluctuations can be found in the CHARMM manual (available from MSI) and hereby incorporated herein by reference.

The molecular dynamics simulation can be carried out using standard charges on the chargeable amino acids. For instance, Asp and Glu is negatively charged and Lys and Arg are positively charged. This condition resembles the medium pH of approximately 7.0. To analyze a lower pH, titration of the molecule can be done to obtain the altered pKa's of the normal titrateable residues within pH 2–10; Lys, Arg, Asp, Glu, Tyr and His. Also Ser, Thr and Cys are titrateable but are not taking into account here. Here the altered charges due to the pH has been described as all Arg, Lys negative at high pH, and all Asp, Glu are uncharged. This imitates a pH around 4 to 5 where the titration Asp and Glu normally takes place.

Model building of the enzyme of interest can be obtained by using the HOMOLOGY model in the MSI program package. The crystal structure of *Aspergillus awamori* variant X100 can be found in, e.g., 3GLY and 1DOG in the Brookhaven database.

EXAMPLES

Example 1

Construction of AMG G2 Variants

Site-directed mutagenesis:

For the construction of variants of AMG G2 (SEQ ID NO: 2) the commercial kit, Chameleon double-stranded, site-directed mutagenesis kit was used according to the manufacturer's instructions.

The gene encoding the AMG G2 enzyme in question is located on pMT838 prepared by deleting the DNA between G2 nt. 1362 and G2 nt. 1530 in plasmid pCAMG91 (see FIG. 1) comprising the AMG G1 form.

In accordance with the manufacturer's instructions the ScaI site of the Ampicillin gene of pMT838 was changed to a MluI site by use of the following primer:

7258: 5'p gaa tga ctt ggt tga cgc gtc acc agt cac 3' (SEQ ID NO: 3).

(Thus changing the ScaI site found in the ampicillin resistance gene and used for cutting to a MluI site). The pMT838 vector comprising the AMG gene in question was then used as a template for DNA polymerase and oligo 7258 (SEQ ID NO: 3) and 21401 (SEQ ID NO: 4).

Primer no. 21401 (SEQ ID NO: 4) was used as the selection primer.

21401: 5'p gg gga tca tga tag gac tag cca tat taa tga agg gca tat acc acg cct tgg acc tgc gtt ata gcc 3'
(Changes the ScaI site found in the AMG gene without changing the amino acid sequence).

The desired mutation (e.g., the introduction of a cystein residue) is introduced into the AMG gene in question by addition of appropriate oligos comprising the desired mutation.

The primer 107581 was used to introduce T12P

107581: 5' pgc aac gaa gcg ccc gtg gct cgt ac 3' (SEQ ID NO: 5)

The mutations are verified by sequencing the whole gene. The plasmid was transformed into *A. oryzae* using the method described above in the "Materials & Methods" section. The variant was fermented and purified as described above in the "Materials & Methods" section.

Example 2

Construction, by Localized Random, Doped Mutagenesis, of *A. niger* AMG Variants Having Improved Thermostability Compared to the Parent Enzyme To improve the thermostability of the *A. niger* AMG random mutagenesis in pre-selected region was performed.

Residue:

Region: L19-G35

Region: A353-V374

The DOPE software (see Materials and Methods) was used to determine spiked codons for each suggested change in the above regions minimizing the amount of stop codons (see table 1). The exact distribution of nucleotides was calculated in the three positions of the codon to give the suggested population of amino acid changes. The doped regions were doped specifically in the indicated positions to have a high chance of getting the desired residues, but still allow other possibilities.

The first column is the amino acid to be mutated, the second column is the percentage of wild type and the third column defined the new amino acid(s).

TABLE 1

| Doping in L19-G35 | | |
|---|---|---|
| L19 | 90% | N |
| N20 | 95% | T |
| N21 | Constant | |
| I22 | Constant | |
| G23 | 95% | A |
| A24 | 90% | S, T |
| D25 | 93% | S, T, R |
| G26 | 95% | A |
| A27 | 90% | S, T |
| W28 | <80% | R, Y |
| V29 | Constant | |
| S30 | 93% | T, N |
| G31 | 95% | A |
| A32 | 95% | V |
| D33 | 80% | R, K, H |
| S34 | 90% | N |
| G35 | Constant | |

The resulting doped oligonucleotide strand is shown in table 2 as sense strand: with the primer sequence, the wild type nucleotide sequence, the parent amino acid sequence and the distribution of nucleotides for each doped position.

TABLE 2

| Position: | 19 | 20 | 21 | 22 | 23 | 24 | 25 | 26 | 27 | 28 | 29 | 30 | 31 | 32 | 33 | 34 | 35 |
|---|---|---|---|---|---|---|---|---|---|---|---|---|---|---|---|---|---|
| A.a. seq.: | L | N | N | I | G | A | D | G | A | W | V | S | G | A | D | S | G |
| primer: | 12T | A3T | AAC | ATC | G4G | 5CG | 67C | G4T | 8CT | 91010 | GTG | 1112C | G4C | G13G | 141516 | 1718T | GGC |
| wt. seq.: | CTG | AAT | AAC | ATC | GGG | GCG | GAC | GGT | GCT | TGG | GTG | TCG | GGC | GCG | GAC | TCT | GGC |

Distribution of nucleotides for each doped position.

1: A10,C90

2: A6,T94

3: A95,C5

4: G95,C5

5: G91,A3,T3,C3

6: G95,A3,C2

7: G3,A95,C2

8: G92,A4,T4

9: A3,T97

10: G95,T5

11: G3,A97

12: G95,A2,C3

13: T5,C95

14: G88,A8,C4

15: G7,A93

16: G4,C96

17: G4,A96

18: G95,A2,C3

Forward primer (SEQ ID NO: 6):

FAMGII '5-C GAA GCG ACC GTG GCT CGT ACT GCC ATC 12T A3T AAC ATC G4G 5CG 67C G4T 8CT 91010 GTG 1112C G4C G13G 141516 1718T GGC ATT GTC GTT GCT AGT CCC AGC ACG GAT AAC-3'

Reverse primer (SEQ ID NO: 7):

RAMG1: 5'-GAT GGC AGT ACG AGC CAC GGT CGC TTC G-3'

TABLE 3

Doping in region A353-V374:

| | | |
|---|---|---|
| A353 | <80% | D, E, Q, N, Y |
| L354 | 90% | Q, E |
| Y355 | 90% | N, Q |
| S356 | 90% | T, D, N |
| G357 | 80% | P, A, S, T |
| A358 | 93% | S |
| A359 | 90% | S, T, N |
| T360 | 90% | R, K |
| G361 | 85% | A, S, T |
| T362 | 90% | S |
| Y363 | Constant | |
| S364 | 93% | D |
| S365 | 93% | N, Q, K |
| S366 | 93% | P, D |
| S367 | Constant | |
| S368 | 93% | D, N, T |
| T369 | 93% | Q, E |
| Y370 | Constant | |
| S371 | 93% | N |
| S372 | 93% | N, T |
| I373 | Constant | |
| V374 | 93% | N, Y, H |

The resulting doped oligonucleotide strand is shown in table 4 as sense strand: with the primer sequence, wild type nucleotide sequence, the parent amino acid sequence and the distribution of nucleotides for each doped position.

TABLE 4

| Position: | 353 | 354 | 355 | 356 | 357 | 358 | 359 | 360 | 361 | 362 | 363 |
|---|---|---|---|---|---|---|---|---|---|---|---|
| A.a. seq.: | A | L | Y | S | D | A | A | T | G | T | Y |
| primer: | 123 | 45A | 6AC | 78C | 910T | 11CT | 1213T | 1415A | 1617C | 18CC | TAC |
| Wt. seq.: | GCA | CTG | TAC | AGC | GAT | GCT | GCT | ACT | GGC | ACC | TAC |
| Pos. (cont.): | 364 | 365 | 366 | 367 | 368 | 369 | 370 | 371 | 372 | 373 | 374 |
| A.a. seq. (cont.): | S | S | S | S | S | T | Y | S | S | I | V |
| primer (cont.): | 1920T | A2122 | 2324C | AGT | 1425C | 2627G | T28T | A16T | 2930T | ATT | 313233 |
| wt. Seq. (cont.): | TCT | TCG | TCC | AGT | TCG | ACT | TAT | AGT | AGC | ATT | GTA |

Distribution of nucleotides for each doped position.
1: G91,A3,T3,C3
2: A13,C87
3: A40,T60
4: G3,A3,C94
5: A6,T94
6: G4,A4,T92
7: G2,A96,C2
8: G93,A3.5,C3.5
9: G87,A8,C5
10: A84,C16
11: G93,T7
12: G92,A5,T3
13: A3,C97
14: G3,A97
15: G2,A2,T4,C92
16: G93,A7
17: G93,C7
18: A90,T10
19: G4,A96
20: G95,A5
21: G96,A4
22: G3,C97
23: G2,A1,T95,C2
24: A3,C97
25: G95,A3,C2
26: G2,A96,C2
27: A5,C95
28: A95,T5
29: G2,A98
30: G94,A4,C2
31: G94,A3,T1,C2
32: A4,T96
33: A20,C80

Primer: FAMGIV (SEQ ID NO: 8)
5'-GTG TCG CTG GAC TTC TTC AAG 123 45A 6AC 78C 910T 11CT 1213T 1415A 1617C 18CC TAC 1920T A2122 2324C AGT 1425C 2627G T28T A16T 2930C ATT 313233 GAT GCC GTG AAG ACT TTC GCC GA-3'

Primer RAMGVI (SEQ ID NO: 9)
5'-ctt gaa gaa gtc cag cga cac-3'

Random Mutagenesis

The spiked oligonucleotides apparent from Table 2 and 3 (which by a common term is designated FAMG) and reverse primers RAMG for the L19-G35 region and specific SEQ ID NO: 2 primers covering the N-terminal (FG2: 5'-CAT CCC CAG GAT CCT TAC TCA GCA ATG-3' (SEQ ID NO: 10) and C-terminal (RG2: 5'-CTC AAA CGA CTC ACC AGC CTC TAG AGT (SEQ ID NO: 11) are used to generate PCR-library-fragments by the overlap extension method (Horton et al., Gene, 77 (1989), pp. 61–68) with an overlap of 21 base pairs. Plasmid pAMGY is template for the Polymerase Chain Reaction. The PCR fragments are cloned by homologous recombination in the E. coli/yeast shuttle vector pAMGY (see Materials and Methods).

Screening

The library was screened in the thermostability filter assays using a Protran filter and incubating at 67–69° C. as described in the "Material & Methods" section above.

Example 3

Construction, by PCR Shuffling Spiked with DNA Oligos, of A. niger AMG Variants Having Improved Thermostability Compared to the Parent Enzyme The polymerase chain reaction (PCR) method was used to prepare DNA fragments carrying the AMG gene and flanking regions. Approximately 10 ug DNA was digested with Dnase, and run on a 2% agarose gel. Fragments of 50–150 bp were purified from the gel. Approximately 1 ug purified fragments were mixed with a 5–15 fold molar excess of oligos carrying the desired mutations. The oligos were of the following kind (for the construction of Hklib1, Hklib2, Hklib3 etc., respectively):

Hklib1:

Hk1-T2X:
5'-ATGTGATTTCCAAGCGCGCGVNNTTGGATTCA-TGGTTGAGCAA

Hk1-N9X:
5'-CCTTGGATTCATGGTTGAGCVNNGAAGCGAC-CGTGGCTCGTAC

Hk1-A11X:
5'-ATTCATGGTTGAGCAACGAAVNNACCGTGGC-TCGTACTGCCAT

Hk1-L66X:
5'-TCCTCAAGACCCTCGTCGATVNNTTCCGAAA-TGGAGATACCAG

Hk1-S386X:
5'-CTTTCGCCGATGGCTTCGTCVNNATTGTGGA-AACTCACGCCGC

Hk1-E389X:
5'-ATGGCTTCGTCTCTATTGTGVNNACTCACGCC-GCAAGCAACGG

Hk1-T390X:
5'-GCTTCGTCTCTATTGTGGAAVNNCACGCCGC-AAGCAACGGCTC

Hk1-A393X:
5'-CTATTGTGGAAACTCACGCCVNNAGCAACGG-CTCCATGTCCGA

Hk1-S394X:
5'-TTGTGGAAACTCACGCCGCAVNNAACGGCTC-CATGTCCGAGCA

Hk1-N395X:
5'-TGGAAACTCACGCCGCAAGCVNNGGCTCCAT-GTCCGAGCAATA

Hk1-G396X:
5'-AAACTCACGCCGCAAGCAACVNNTCCATGTC-CGAGCAATACGA

Hk1-K404X:
5'-CCATGTCCGAGCAATACGACVNNTCTGATGG-CGAGCAGCTTTC (SEQ ID NO:14)

Hk1-D406X:
5'-CCGAGCAATACGACAAGTCTVNNGGCGAGC-AGCTTTCCGCTCG (SEQ ID NO:15)

Hk1-E408X:
5'-AATACGACAAGTCTGATGGCVNNCAGCTTTC-CGCTCGCGACCT (SEQ ID NO:16)

Hk1-L410X:
5'-ACAAGTCTGATGGCGAGCAGVNNTCCGCTC-GCGACCTGACCT (SEQ ID NO:17)

Hk1-L423X:
5'-CCTGGTCTTATGCTGCTCTGVNNACCGCCAA-CAACCGTCGTAA (SEQ ID NO:18)

Hk1-N426X:
5'-ATGCTGCTCTGCTGACCGCCVNNAACCGTCG-TAACTCCGTCGTG (SEQ ID NO:19)

Hk1-N427X:
5'-CTGCTCTGCTGACCGCCAACVNNCGTCGTAA-CTCCGTCGTGCCT (SEQ ID NO:20)

Hk1-Y402X:
5'-ACGGCTCCATGTCCGAGCAANNCGACAAGT-CTGATGGCGAGCAGCT (SEQ ID NO:21)

Hklib2:

Hk2-L234X-SENSE:
5'-CTGGACCGGCAGCTTCATTNNKGCCAACTTC-GATAGCAGCC (SEQ ID NO:22)

Hk2-A235S-ANTISENSE:
5'-GAACGGCTGCTATCGAAGTTAGACAGAATGA-AGCTGCCGGTC

Hk2-F237X-SENSE:
5-CAGCTTCATTCTGGCCAACNATGATAGCAGCC-GTTCCGGCA (SEQ ID NO:23)

Hk2-D238T-ANTISENSE:
5'-CCTTGCCGGAACGGCTGCTAGTGAAGTTGGC-CAGAATGAAGC (SEQ ID NO:24)

Hk2-D238S-ANTISENSE:
5'-CCTTGCCGGAACGGCTGCTAGAGAAGTTGGC-CAGAATGAAGC (SEQ ID NO:25)

Hk2-S239X-SENSE:
5'-TCATTCTGGCCAACTTCGATNNCAGCCGTTCC-GGCAAGGACG (SEQ ID NO:26)

Hk2-S240G-ANTISENSE:
5'-TTGCGTCCTTGCCGGAACGACCGCTATCGAA-GTTGGCCAGAA (SEQ ID NO:27)

Hk2-S242X-ANTISENSE:
5'-GGGTGTTTGCGTCCTTGCCAKNACGGCTGCT-ATCGAAGTTG (SEQ ID NO:28)

Hk2-G243X-ANTISENSE:
5'-GGAGGGTGTTTGCGTCCTTAKNGGAACGGCT-GCTATCGAAG (SEQ ID NO:29)

Hk2-K244R-SENSE:
5'-CGATAGCAGCCGTTCCGGCAGAGACGCAAAC-ACCCTCCTGG (SEQ ID NO:30)

Hk2-T310V-ANTISENSE:
5'-ACGGGTTGCCGTTGTAGTAAACGTCCTCAGG-GTACCGACCC (SEQ ID NO:31)

Hk2-T310S-ANTISENSE:
5'-ACGGGTTGCCGTTGTAGTAAGAGTCCTCAGG-GTACCGACCC (SEQ ID NO:32)

Hk2-Y311N-SENSE:
5'-TCGGTACCCTGAGGACACGAATTACAACGGC-AACCCGTGGT (SEQ ID NO:33)

Hk2-Y312Q-ANTISENSE:
5'-GGAACCACGGGTTGCCGTTTTGGTACGTGTC-CTCAGGGTAC (SEQ ID NO:34)

Hk2-Y312N-ANTISENSE:
5'-GGAACCACGGGTTGCCGTTATTGTACGTGTC-CTCAGGGTAC (SEQ ID NO:35)

Hk2-N313T-SENSE:
5'-CCCTGAGGACACGTACTACACTGGCAACCC-GTGGTTCCTGT (SEQ ID NO:36)

Hk2-N313S-SENSE:
5'-CCCTGAGGACACGTACTACTCTGGCAACCCG-TGGTTCCTGT (SEQ ID NO:37)

Hk2-N313G-SENSE:
5'-CCCTGAGGACACGTACTACGGTGGCAACCCG-TGGTTCCTGT (SEQ ID NO:38)

Hk2-N315Q-ANTISENSE:
5'-AGGTGCACAGGAACCACGGTTGGCCGTTGTA-GTACGTGTCC (SEQ ID NO:39)

Hk2-N315E-ANTISENSE:
5'-AGGTGCACAGGAACCACGGTTCGCCGTTGTA-GTACGTGTCC (SEQ ID NO:40)

Hk2-N315R-ANTISENSE:
5'-AGGTGCACAGGAACCACGGTCTGCCGTTGTA-GTACGTGTCC (SEQ ID NO:41)

Hk2F318Y-ANTISENSE:
5'-CGGCAGCCAAGGTGCACAGATACCACGGGTT-GCCGTTGTAG (SEQ ID NO:42)

Hk2-Q409P-SENSE:
  5'-CGACAAGTCTGATGGCGAGCCACTTTCCGCT-CGCGACCTGA (SEQ ID NO:43)
Hklib3:
Hk3-D336X-SENSE: (SEQ ID NO:44)
  5'-CGATGCTCTATACCAGTGGNNKAAGCAGGGG-TCGTTGGAGG
Hk3-K337X-SENSE:
  5'-TGCTCTATACCAGTGGGACNNKCAGGGGTCG-TTGGAGGTCA (SEQ ID NO:45)
Hk3-Q338X-ANTISENSE:
  5'-CTGTGACCTCCAACGACCCGNNCTTGTCCCA-CTGGTATAGA (SEQ ID NO:46)
Hk3-G339X-SENSE:
  5'-ATACCAGTGGGACAAGCAGNCUTCGTTGGAG-GTCACAGATG (SEQ ID NO:47)
Hk3-S340X'-ANTISENSE:
  5'-ACACATCTGTGACCTCCAAANTCCCCTGCTT-GTCCCACTGG (SEQ ID NO:48)
Hk3-S340X''-ANTISENSE:
  40 5'-ACACATCTGTGACCTCCAAANCCCCTGCT-TGTCCCACTGG (SEQ ID NO:49)
Hk3-L341X-SENSE:
  5'-GTGGGACAAGCAGGGGTCGNUUGAGGTCAC-AGATGTGTCGC (SEQ ID NO:50)
Hk3-K352Q-SENSE:
  5'-TGTGTCGCTGGACTTCTTCCAAGCACTGTAC-AGCGATGCTG (SEQ ID NO:51)
Hk3-K352R-SENSE:
  5'-TGTGTCGCTGGACTTCTTCAGAGCACTGTAC-AGCGATGCTG (SEQ ID NO:52)
Hk3-A353D-ANTISENSE:
  5'-TAGCAGCATCGCTGTACAGATCCTTGAAGAA-GTCCAGCGAC (SEQ ID NO:53)
Hk3-A353S-ANTISENSE:
  5'-TAGCAGCATCGCTGTACAGAGACTTGAAGAA-GTCCAGCGAC (SEQ ID NO:54)
Hk3-S356P-SENSE:
  5'-ACTTCTTCAAGGCACTGTACCCAGATGCTGCT-ACTGGCACCT (SEQ ID NO:55)
Hk3-S356N-SENSE:
  5'-ACTTCTTCAAGGCACTGTACAAUGATGCTGCT-ACTGGCACCTA (SEQ ID NO:56)
Hk3-S356D-SENSE:
  5'-ACTTCTTCAAGGCACTGTACGAUGATGCTGC-TACTGGCACCTA (SEQ ID NO:57)
Hk3-D357S-ANTISENSE:
  5'-GAGTAGGTGCCAGTAGCAGCAGAGCTGTACA-GTGCCTTGAAGA (SEQ ID NO:58)
Hk3-A359S-SENSE:
  5'-GGCACTGTACAGCGATGCTTCTACTGGCACC-TACTCTTCGT (SEQ ID NO:59)
Hk3-T360V-ANTISENSE:
  5'-TGGACGAAGAGTAGGTGCCAACAGCAGCATC-GCTGTACAGT (SEQ ID NO:60)
Hk3-G361X-SENSE:
  5'-TGTACAGCGATGCTGCTACTNCTACCTACTCT-TCGTCCAGTTC (SEQ ID NO:61)
Hk3-T362R-ANTISENSE:
  5'-GTCGAACTGGACGAAGAGTATCTGCCAGTAG-CAGCATCGCTG (SEQ ID NO:62)
Hk3-S364X-SENSE:
  5'-TGCTGCTACTGGCACCTACNNKTCGTCCAGT-TCGACTTATAG (SEQ ID NO:63)
Hk3-S365X-SENSE:
  5'-TGCTACTGGCACCTACTCTNNKTCCAGTTCGA-CTTATAGTAG (SEQ ID NO:65)
Hk3-S366T-ANTISENSE:
  5'-ATGCTACTATAAGTCGAACTAGTCGAAGAGTA-GGTGCCAGTA (SEQ ID NO:66)
Hk3-S368X-ANTISENSE:
  5'-TCTACAATGCTACTATAAGTAGNACTGGACGA-AGAGTAGGTG (SEQ ID NO:67)
Hk3-T369X-SENSE:
  5'-CTACTCTTCGTCCAGTTCGNNKTATAGTAGCA-TTGTAGATGCC (SEQ ID NO:68)
Hk3-S371X-ANTISENSE:
  5'-TTCACGGCATCTACAATGCTATNATAAGTCGA-ACTGGACGAAG (SEQ ID NO:69)
Hk3-S372X-SENSE:
  5'-CGTCCAGTTCGACTTATAGTNNTATTGTAGAT-GCCGTGAAGAC (SEQ ID NO:70)

To the mix of Dnase treated DNA and oligos was added nucleotides, PCR buffer and Taq/Pwo polymerase. A PCR assembly reaction was performed, using first 94° C. for 2 min., then 35–40 cycles with the following incubation times: 94° C., 30 sec.; 45° C., 30 sec.; 72° C., 60 sec; then finally 72° C. for 5 min. An PCR amplification reaction was performed with 1 uL of the assembly reaction as template, and adding primers that anneal to the regions flanking the AMG gene. Parameters: first 94° C. for 2 min., then 35–40 cycles with the following incubation times: 94° C., 30 sec.; 55° C., 30 sec.; 72° C., 90 sec; then finally 72° C. for 10 min.

The resulting PCR product was purified from a 1% agarose gel, mixed with linearized vector and transformed into competent yeast cells, as described above.

Example 4

Specific Activity

AMG G2 variants were constructed as described above in Example 1. The specific activity as $k_{cat}$ were measured on purified samples at pH 4.3, 37° C., using maltose and maltohepatose as substrate as described in the "Materials & Methods" section above. The specific activity as AGU/mg were also measured at pH 4.3, 37° C., using maltose as substrate as described in the "Materials & Methods" section above.

|  | Kcat (sec. −1) | | |
| --- | --- | --- | --- |
| Variant | Maltose | Malto-heptaose | AGU/mg |
| AMG G2 (wild type) | 6.0 | 38 | 1.8 |
| N110T | 9.7 | 27.8 | 3.5 |
| V111P | 12.0 | 43.2 | 3.1 |
| S119P | 6.2 | 44.0 | 2.1 |
| G127A | 21.0 | 40.0 | 5.8 |
| G207N | 30.5 | 36.3 | 5.7 |
| L3N |  |  | 2.3 |
| S56A |  |  | 2.6 |
| A102* |  |  | 2.5 |
| D403S |  |  | 2.2 |
| I18V+T51S+S56A+V59T+L60A |  |  | 3.3 |
| S119P+Y402F |  |  | 2.7 |
| S119P+I189T+Y223F+F227Y+Y402F |  |  | 3.0 |

Example 5

Thermostability at 70° C.

An AMG G2 S119P variant was constructed using the approach described in Example 1.

The thermostability was determined as $T_{1/2}$ using Method I, and as % residual activity after incubation for 30 minutes in 50 mM NaOAc, pH 4.5, 70° C., 0.2 AGU/ml, as described in the "Material & Methods" section above. The result of the tests are in the Table below and compared to the wild-type *A. niger* AMG G2.

| *A. niger* AMG (Enzyme) | Residual activity (%) | T½ (min.) |
|---|---|---|
| S119P variant | 22 | 17 |
| wild-type (SEQ ID NO: 2) | 13 | 8 |

Example 6

Thermostability at 68° C.

AMG2 variants were constructed using the approach described in Example 3, except for variants Nos. 1 and 2 in the Table below, which were prepared by shuffling as described in WO 95/22625 (from Affymax Technologies N.V.).

The thermostability was determined as T½ using method I at 68° C. as described in the "Materials & Methods" section and compared to the wild-type *A. niger* AMG G2 under the same conditions. Evaluation of variants were performed on culture broth after filtration of the supernatants.

| | Variant | T½ (min) | T½ *A. niger* AMG G2 (wild type) (min) |
|---|---|---|---|
| 1 | A246T + T72I | 11.3 | 8.5 |
| 2 | G447S + S119P | 11.4 | 7.9 |
| 3 | E408R + A425T + S465P + T494A | 8.6 | 8.1 |
| 4 | E408R + S386N | 12.6 | 8.9 |
| 5 | T2P | 9.3 | 8.5 |
| 6 | T2Q + A11P + S394R | 10.7 | 8.5 |
| 7 | T2H | 9.5 | 8.9 |
| 8 | A11E + E408R | 12.7 | 9.3 |
| 9 | T2M + N9A + T390R + D406N + L410R | 10.7 | 8.5 |
| 10 | A393R | 17.7 | 8.4 |
| 11 | T2R + S386R + A393R | 14.1 | 8.4 |
| 12 | A393R + L410R | 14.7 | 7.9 |
| 13 | A1V + L66R + Y402F + N427S + S486G | 11.7 | 8.5 |
| 14 | T2K + S30P + N427M + S444G + V470M | 11.4 | 8.4 |

Thermostability at 70° C. on purified samples.

| | Enzyme | T½ (min) |
|---|---|---|
| 15 | AMG G2 (wild type) | 7.4 |
| 16 | T2E + T379A + S386K + A393R | 11.6 |
| 17 | E408R + S386N | 10.2 |
| 18 | T2Q + A11P + S394R | 9.8 |
| 19 | A1V + L66R + Y402F + N427S + S486G | 14.1 |
| 20 | A393R | 14.6 |
| 21 | T2R + S386R + A393R | 14.1 |
| 22 | A393R + L410R | 12.9 |
| 23 | Y402F | 10.1 |

Example 7

Thermostability at 68° C.

AMG G2 variants were constructed by shuffling using the approach described in Example 3 followed by shuffling of positive variants.

The thermosostability was determined as T½ using method I at 68° C. as described in the "Materials & Methods" section and compared to the wild-type *A. niger* AMG G2 under the same conditions. Evaluation of variants were performed on culture broth after filtration of the supernatants.

| | Variant | T½ (min) | T½ *A. niger* AMG G2 (wild type) (min) |
|---|---|---|---|
| 24 | PLASD[i]+V59A+A393R+T490A | 27.2 | 6.8 |

[i]N-terminal extension

Example 8

Thermostability at 68° C.

AMG G2 variants were constructed using the approach described in Example 3. The thermostability was determined as T½ using method I at 68° C. as described in the "Materials & Methods" section and compared to the wild-type *A. niger* AMG G2 under the same conditions. Evaluation of variants were performed on culture broth after filtration of the supernatants.

| | Variant | T½ (min) | T½ *A. niger* AMG G2 wild-type (min) |
|---|---|---|---|
| 25 | D357S + T360V + S371H | 6.6 | 5.9 |
| 26 | N313G + F318Y | 8.9 | 5.9 |
| 27 | S356P + S366T | 7.3 | 5.8 |
| 28 | S340G + D357S + T360V + S386P | 7.2 | 5.8 |

Example 9

Thermostability at 70° C.

An AMG G2 variants was constructed using the approach described in Example 1 and evaluated as semi-purified (filtration of culture broth followed by desalting on a G-25 column) samples.

The thermostability was determined as % residual activity using Method I in 50 mM NaOAc, pH 4.5, 70° C., as described in the "Material & Methods" section above. The result of the test is listed in the Table below and compared to the wild-type *A. niger* AMG G2.

| | Enzyme | T½ (min) |
|---|---|---|
| 29 | AMG G2 (wild type) | 7 |
| 30 | Y402F + S411V | 60 |
| 31 | S119P + Y402F + S411V | 115 |
| 32 | S119P + Y312Q + Y402F + T416H | 50 |

Example 10

Thermostability at 70° C. in Presence of 30% Glucose

AMG G2 variants were constructed using the approach described in Example 3.

The thermostability was determined as T½ using method II at 70° C. as described in the "Materials & Methods" section and compared to the wild-type *A. niger* AMG G2 under the same conditions.

| | Enzyme | T½ (hr) |
|---|---|---|
| 33 | AMG G2 (wild type) | 1.5 |
| 34 | Y402F | 2.5 |
| 35 | A393R | 4.0 |
| 36 | T2R + S386R + A393R | 2.0 |
| 37 | PLASD (N-terminal) + V59A + A393R + T490A | 16.0 |

Example 11

Saccharification Performance of AMG Variants S119P+Y402F+S411V and PLASD(N-terminal)+V59A+A393R+T490A, Respectively Saccharification performance of the AMG variants S119P+Y402F+S411V and PLASD(N-terminal)+V59A+A393R+T490A, respectively, both having improved thermostability are tested at 70° C. as described below.

Reference enzyme is the wild-type *A. niger* AMG G2. Saccharification is run under the following conditions:

| | |
|---|---|
| Substrate | 10 DE Maltodextrin, approx. 30% DS (w/w) |
| Temperature | 70° C. |
| Initial pH | 4.3 (at 70° C.) |
| Enzyme dosage | 0.24 AGU/g DS |

Saccharification

The substrate for saccharification is made by dissolving maltodextrin (prepared from common corn) in boiling Milli-Q water and adjusting the dry substance to approximately 30% (w/w). pH is adjusted to 4.3. Aliquots of substrate corresponding to 15 g dry solids are transferred to 50 ml blue cap glass flasks and placed in a water bath with stirring. Enzymes are added and pH re-adjusted if necessary. The experiment is run in duplicate. Samples are taken periodically and analysed at HPLC for determination of the carbohydrate composition.

What is claimed is:

1. An isolated variant of a parent glucoamylase comprising one or more mutations in the following positions in the amino acid sequence shown in SEQ ID NO:2 or in a corresponding position in a homologous glucoamylase having at least 60% homology with the amino acid sequence shown in SEQ ID NO:2:

1, 2, 3, 4, 5, 6, 7, 8, 9, 10, 11, 12, 13, 14, 15, 16, 17, 18, 19, 21, 22, 23, 24, 25, 26, 28, 29, 31, 32, 33, 34, 35, 40, 41, 42, 43, 44, 45, 46, 47, 49, 51, 53, 56, 58, 59, 60, 61, 62, 73, 74, 75, 76, 77, 78, 79, 80, 93, 94, 95, 96, 97, 98, 99, 100, 101, 102, 103, 104, 105, 106, 107, 109, 110, 111, 113, 114, 115, 117, 118, 126, 127, 200, 201, 202, 203, 204, 205, 206, 207, 208, 209, 210, 211, 234, 235, 237, 238, 239, 240, 242, 243, 244, 245, 287, 288, 289, 290, 291, 292, 294, 295, 296, 297, 298, 299, 300, 301, 303, 304, 307, 308, 310, 311, 313, 314, 315, 316, 318, 319, 334, 335, 336, 337, 338, 339, 340, 341, 353, 354, 355, 356, 357, 358, 359, 360, 361, 362, 363, 363, 365, 366, 367, 368, 369, 370, 371, 372, 373, 374, 388, 390, 394, 397, 398, 399, 402, 403, 404, 405, 406, 409, 412, 413, 414, 445, 446, 447, 448, 449, 450, 451, 452, 453, 454, 455, 456, 457, 458, 459, 461, 462, 463, 464, 465, 466, 467, 468, 469, 470.

2. The variant of claim 1, wherein the variant comprise one or more of the following mutations in the amino acid sequence shown in SEQ ID NO:2 or in a corresponding position in a homologous glucoamylase having at least 60% homology with the amino acid sequence shown in SEQ ID NO:2: A1V, T2E/P/Q/R/H/M, L3P/N, N9A, A11P/E, I18V, L19N, G23A, A24S/T, D25S/T/R, G26A, W28R/Y, G31A, A32V, D33R/K/H, S34N, S40C, T43R, T51D/S, T53D, S56A/C, V59T/A, L60A, N93T, P94V, S95N, D97S, L98P/S, S100T/D, A102S/*, N110T, V111P, E113M/A, T114S, A115Q/G, G127A, A201D, F202L, A203L, T204K, A205R/S, V206L/N, G207N, S208H/T/D, S209T, S211P, N313T/S/G, A353D/S, S356P/N/D, D357S, A359S, T360V, G361S/P/T/A, T362R, S364A/R/N/D/C/Q/E/G/H/I/L/K/M/F/P/T/W/Y/V, S365A/R/N/D/C/Q/E/G/H/I/L/K/M/F/P/T/W/Y/V, S366T, S368P/T/A, T369A/R/N/D/C/Q/E/G/H/I/L/K/M/F/P/T/W/Y/V, S371Y/H/N/D, S372F/Y/C/L/P/H/R/I/T/N/S/V/A/D/G, T390R, S394R/P, M398L, S399C/Q/T, Y402F, D403S, S405T, D406N, A412C, D414A, G447S, S465P.

3. The variant of claim 1, wherein the variant comprises one or more mutations in the following positions in the amino acid sequence shown in SEQ ID NO:2 or in a corresponding position in a homologous glucoamylase having at least 60% homology with the amino acid sequence shown in SEQ ID NO:2: 287, 288, 289, 290, 291, 292, 294, 295, 296, 297, 298, 299, 300, 307, 308, 310, 311, 313, 314, 315, 316, 318, 319.

4. The variant of claim 1, wherein the homologous glucoamylase is the *Aspergillus niger* G1 glucoamylase.

5. The variant of claim 1, wherein the glucoamylase is a truncated glucoamylase.

6. The variant of claim 5, wherein the truncation is at a C-terminal amino acid.

* * * * *

SEQUENCE LISTING

```
<160> NUMBER OF SEQ ID NOS: 81

<210> SEQ ID NO 1
<211> LENGTH: 1605
<212> TYPE: DNA
<213> ORGANISM: Aspergillus niger
<220> FEATURE:
<221> NAME/KEY: sig_peptide
<222> LOCATION: (1)...(72)
<221> NAME/KEY: mat_peptide
<222> LOCATION: (73)...(1602)
<221> NAME/KEY: CDS
<222> LOCATION: (1)...(1602)

<400> SEQUENCE: 1 atg tcg ttc cga tct cta ctc gcc ctg agc ggc ctc gtc tgc aca ggg      48
Met Ser Phe Arg Ser Leu Leu Ala Leu Ser Gly Leu Val Cys Thr Gly
            -20                 -15                 -10 ttg gca aat gtg att tcc aag cgc gcg acc ttg gat tca tgg ttg agc      96
Leu Ala Asn Val Ile Ser Lys Arg Ala Thr Leu Asp Ser Trp Leu Ser
        -5                   1               5 aac gaa gcg acc gtg gct cgt act gcc atc ctg aat aac atc ggg gcg     144
Asn Glu Ala Thr Val Ala Arg Thr Ala Ile Leu Asn Asn Ile Gly Ala
         10                  15                  20 gac ggt gct tgg gtg tcg ggc gcg gac tct ggc att gtc gtt gct agt     192
Asp Gly Ala Trp Val Ser Gly Ala Asp Ser Gly Ile Val Val Ala Ser
 25                  30                  35                  40 ccc agc acg gat aac ccg gac tac ttc tac acc tgg act cgc gac tct     240
Pro Ser Thr Asp Asn Pro Asp Tyr Phe Tyr Thr Trp Thr Arg Asp Ser
                     45                  50                  55 ggt ctc gtc ctc aag acc ctc gtc gat ctc ttc cga aat gga gat acc     288
Gly Leu Val Leu Lys Thr Leu Val Asp Leu Phe Arg Asn Gly Asp Thr
             60                  65                  70 agt ctc ctc tcc acc att gag aac tac atc tcc gcc cag gca att gtc     336
Ser Leu Leu Ser Thr Ile Glu Asn Tyr Ile Ser Ala Gln Ala Ile Val
         75                  80                  85 cag ggt atc agt aac ccc tct ggt gat ctg tcc agc ggc gct ggt ctc     384
Gln Gly Ile Ser Asn Pro Ser Gly Asp Leu Ser Ser Gly Ala Gly Leu
 90                  95                 100
```

-continued

| | |
|---|---|
| ggt gaa ccc aag ttc aat gtc gat gag act gcc tac act ggt tct tgg<br>Gly Glu Pro Lys Phe Asn Val Asp Glu Thr Ala Tyr Thr Gly Ser Trp<br>105                      110                    115                      120 | 432 |
| gga cgg ccg cag cga gat ggt ccg gct ctg aga gca act gct atg atc<br>Gly Arg Pro Gln Arg Asp Gly Pro Ala Leu Arg Ala Thr Ala Met Ile<br>                      125                    130                    135 | 480 |
| ggc ttc ggg cag tgg ctg ctt gac aat ggc tac acc agc acc gca acg<br>Gly Phe Gly Gln Trp Leu Leu Asp Asn Gly Tyr Thr Ser Thr Ala Thr<br>          140                    145                    150 | 528 |
| gac att gtt tgg ccc ctc gtt agg aac gac ctg tcg tat gtg gct caa<br>Asp Ile Val Trp Pro Leu Val Arg Asn Asp Leu Ser Tyr Val Ala Gln<br>              155                    160                    165 | 576 |
| tac tgg aac cag aca gga tat gat ctc tgg gaa gaa gtc aat ggc tcg<br>Tyr Trp Asn Gln Thr Gly Tyr Asp Leu Trp Glu Glu Val Asn Gly Ser<br>170                      175                    180 | 624 |
| tct ttc ttt acg att gct gtg caa cac cgc gcc ctt gtc gaa ggt agt<br>Ser Phe Phe Thr Ile Ala Val Gln His Arg Ala Leu Val Glu Gly Ser<br>185                      190                    195                  200 | 672 |
| gcc ttc gcg acg gcc gtc ggc tcg tcc tgc tcc tgg tgt gat tct cag<br>Ala Phe Ala Thr Ala Val Gly Ser Ser Cys Ser Trp Cys Asp Ser Gln<br>                    205                    210                    215 | 720 |
| gca ccc gaa att ctc tgc tac ctg cag tcc ttc tgg acc ggc agc ttc<br>Ala Pro Glu Ile Leu Cys Tyr Leu Gln Ser Phe Trp Thr Gly Ser Phe<br>              220                    225                    230 | 768 |
| att ctg gcc aac ttc gat agc agc cgt tcc ggc aag gac gca aac acc<br>Ile Leu Ala Asn Phe Asp Ser Ser Arg Ser Gly Lys Asp Ala Asn Thr<br>235                      240                    245 | 816 |
| ctc ctg gga agc atc cac acc ttt gat cct gag gcc gca tgc gac gac<br>Leu Leu Gly Ser Ile His Thr Phe Asp Pro Glu Ala Ala Cys Asp Asp<br>          250                    255                    260 | 864 |
| tcc acc ttc cag ccc tgc tcc ccg cgc gcg ctc gcc aac cac aag gag<br>Ser Thr Phe Gln Pro Cys Ser Pro Arg Ala Leu Ala Asn His Lys Glu<br>265                      270                    275                  280 | 912 |
| gtt gta gac tct ttc cgc tca atc tat acc ctc aac gat ggt ctc agt<br>Val Val Asp Ser Phe Arg Ser Ile Tyr Thr Leu Asn Asp Gly Leu Ser<br>                    285                    290                    295 | 960 |
| gac agc gag gct gtt gcg gtg ggt cgg tac cct gag gac acg tac tac<br>Asp Ser Glu Ala Val Ala Val Gly Arg Tyr Pro Glu Asp Thr Tyr Tyr<br>              300                    305                    310 | 1008 |
| aac ggc aac ccg tgg ttc ctg tgc acc ttg gct gcc gca gag cag ttg<br>Asn Gly Asn Pro Trp Phe Leu Cys Thr Leu Ala Ala Ala Glu Gln Leu<br>                    315                    320                    325 | 1056 |
| tac gat gct cta tac cag tgg gac aag cag ggg tcg ttg gag gtc aca<br>Tyr Asp Ala Leu Tyr Gln Trp Asp Lys Gln Gly Ser Leu Glu Val Thr<br>330                      335                    340 | 1104 |
| gat gtg tcg ctg gac ttc ttc aag gca ctg tac agc gat gct gct act<br>Asp Val Ser Leu Asp Phe Phe Lys Ala Leu Tyr Ser Asp Ala Ala Thr<br>345                      350                    355                  360 | 1152 |
| ggc acc tac tct tcg tcc agt tcg act tat agt agc att gta gat gcc<br>Gly Thr Tyr Ser Ser Ser Ser Thr Tyr Ser Ser Ile Val Asp Ala<br>                    365                    370                    375 | 1200 |
| gtg aag act ttc gcc gat ggc ttc gtc tct att gtg gaa act cac gcc<br>Val Lys Thr Phe Ala Asp Gly Phe Val Ser Ile Val Glu Thr His Ala<br>              380                    385                    390 | 1248 |
| gca agc aac ggc tcc atg tcc gag caa tac gac aag tct gat ggc gag<br>Ala Ser Asn Gly Ser Met Ser Glu Gln Tyr Asp Lys Ser Asp Gly Glu<br>395                      400                    405 | 1296 |
| cag ctt tcc gct cgc gac ctg acc tgg tct tat gct gct ctg ctg acc<br>Gln Leu Ser Ala Arg Asp Leu Thr Trp Ser Tyr Ala Ala Leu Leu Thr | 1344 |

-continued

| | | | | 410 | | | | 415 | | | | 420 | | | |
|---|---|---|---|---|---|---|---|---|---|---|---|---|---|---|---|
| gcc | aac | aac | cgt | cgt | aac | tcc | gtc | gtg | cct | gct | tct | tgg | ggc | gag | acc | 1392
| Ala | Asn | Asn | Arg | Arg | Asn | Ser | Val | Val | Pro | Ala | Ser | Trp | Gly | Glu | Thr |
| 425 | | | | 430 | | | | 435 | | | | 440 | | | |

| tct | gcc | agc | agc | gtg | ccc | ggc | acc | tgt | gcg | gcc | aca | tct | gcc | att | ggt | 1440
|---|---|---|---|---|---|---|---|---|---|---|---|---|---|---|---|
| Ser | Ala | Ser | Ser | Val | Pro | Gly | Thr | Cys | Ala | Ala | Thr | Ser | Ala | Ile | Gly |
| | | | | 445 | | | | 450 | | | | | 455 | | |

| acc | tac | agc | agt | gtg | act | gtc | acc | tcg | tgg | ccg | agt | atc | gtg | gct | act | 1488
|---|---|---|---|---|---|---|---|---|---|---|---|---|---|---|---|
| Thr | Tyr | Ser | Ser | Val | Thr | Val | Thr | Ser | Trp | Pro | Ser | Ile | Val | Ala | Thr |
| | | | 460 | | | | | 465 | | | | 470 | | | |

| ggc | ggc | acc | act | acg | acg | gct | acc | ccc | act | gga | tcc | ggc | agc | gtg | acc | 1536
|---|---|---|---|---|---|---|---|---|---|---|---|---|---|---|---|
| Gly | Gly | Thr | Thr | Thr | Thr | Ala | Thr | Pro | Thr | Gly | Ser | Gly | Ser | Val | Thr |
| | | 475 | | | | | 480 | | | | | 485 | | | |

| tcg | acc | agc | aag | acc | acc | gcg | act | gct | agc | aag | acc | agc | acc | acg | acc | 1584
|---|---|---|---|---|---|---|---|---|---|---|---|---|---|---|---|
| Ser | Thr | Ser | Lys | Thr | Thr | Ala | Thr | Ala | Ser | Lys | Thr | Ser | Thr | Thr | Thr |
| | 490 | | | | 495 | | | | | 500 | | | | | |

| cgc | tct | ggt | atg | tca | ctg | tga | | | | | | | | | | 1605
|---|---|---|---|---|---|---|---|---|---|---|---|---|---|---|---|
| Arg | Ser | Gly | Met | Ser | Leu | | | | | | | | | | |
| 505 | | | | 510 | | | | | | | | | | | |

<210> SEQ ID NO 2
<211> LENGTH: 534
<212> TYPE: PRT
<213> ORGANISM: Aspergillus niger
<220> FEATURE:
<221> NAME/KEY: SIGNAL
<222> LOCATION: (1)...(24)

<400> SEQUENCE: 2

Met Ser Phe Arg Ser Leu Leu Ala Leu Ser Gly Leu Val Cys Thr Gly
                -20                 -15                 -10

Leu Ala Asn Val Ile Ser Lys Arg Ala Thr Leu Asp Ser Trp Leu Ser
            -5                   1               5

Asn Glu Ala Thr Val Ala Arg Thr Ala Ile Leu Asn Asn Ile Gly Ala
        10                  15                  20

Asp Gly Ala Trp Val Ser Gly Ala Asp Ser Gly Ile Val Val Ala Ser
25                  30                  35                  40

Pro Ser Thr Asp Asn Pro Asp Tyr Phe Tyr Thr Trp Thr Arg Asp Ser
                45                  50                  55

Gly Leu Val Leu Lys Thr Leu Val Asp Leu Phe Arg Asn Gly Asp Thr
            60                  65                  70

Ser Leu Leu Ser Thr Ile Glu Asn Tyr Ile Ser Ala Gln Ala Ile Val
        75                  80                  85

Gln Gly Ile Ser Asn Pro Ser Gly Asp Leu Ser Ser Gly Ala Gly Leu
    90                  95                  100

Gly Glu Pro Lys Phe Asn Val Asp Glu Thr Ala Tyr Thr Gly Ser Trp
105                 110                 115                 120

Gly Arg Pro Gln Arg Asp Gly Pro Ala Leu Arg Ala Thr Ala Met Ile
                125                 130                 135

Gly Phe Gly Gln Trp Leu Leu Asp Asn Gly Tyr Thr Ser Thr Ala Thr
            140                 145                 150

Asp Ile Val Trp Pro Leu Val Arg Asn Asp Leu Ser Tyr Val Ala Gln
        155                 160                 165

Tyr Trp Asn Gln Thr Gly Tyr Asp Leu Trp Glu Glu Val Asn Gly Ser
    170                 175                 180

Ser Phe Phe Thr Ile Ala Val Gln His Arg Ala Leu Val Glu Gly Ser
185                 190                 195                 200

-continued

```
Ala Phe Ala Thr Ala Val Gly Ser Ser Cys Ser Trp Cys Asp Ser Gln
            205                 210                 215
Ala Pro Glu Ile Leu Cys Tyr Leu Gln Ser Phe Trp Thr Gly Ser Phe
            220                 225                 230
Ile Leu Ala Asn Phe Asp Ser Arg Ser Gly Lys Asp Ala Asn Thr
            235                 240                 245
Leu Leu Gly Ser Ile His Thr Phe Asp Pro Glu Ala Ala Cys Asp Asp
    250                 255                 260
Ser Thr Phe Gln Pro Cys Ser Pro Arg Ala Leu Ala Asn His Lys Glu
265                 270                 275                 280
Val Val Asp Ser Phe Arg Ser Ile Tyr Thr Leu Asn Asp Gly Leu Ser
                285                 290                 295
Asp Ser Glu Ala Val Ala Val Gly Arg Tyr Pro Glu Asp Thr Tyr Tyr
            300                 305                 310
Asn Gly Asn Pro Trp Phe Leu Cys Thr Leu Ala Ala Ala Glu Gln Leu
            315                 320                 325
Tyr Asp Ala Leu Tyr Gln Trp Asp Lys Gln Gly Ser Leu Glu Val Thr
    330                 335                 340
Asp Val Ser Leu Asp Phe Phe Lys Ala Leu Tyr Ser Asp Ala Ala Thr
345                 350                 355                 360
Gly Thr Tyr Ser Ser Ser Ser Thr Tyr Ser Ser Ile Val Asp Ala
                365                 370                 375
Val Lys Thr Phe Ala Asp Gly Phe Val Ser Ile Val Glu Thr His Ala
            380                 385                 390
Ala Ser Asn Gly Ser Met Ser Glu Gln Tyr Asp Lys Ser Asp Gly Glu
            395                 400                 405
Gln Leu Ser Ala Arg Asp Leu Thr Trp Ser Tyr Ala Ala Leu Leu Thr
    410                 415                 420
Ala Asn Asn Arg Arg Asn Ser Val Val Pro Ala Ser Trp Gly Glu Thr
425                 430                 435                 440
Ser Ala Ser Ser Val Pro Gly Thr Cys Ala Ala Thr Ser Ala Ile Gly
                445                 450                 455
Thr Tyr Ser Ser Val Thr Val Thr Ser Trp Pro Ser Ile Val Ala Thr
            460                 465                 470
Gly Gly Thr Thr Thr Thr Ala Thr Pro Thr Gly Ser Gly Ser Val Thr
            475                 480                 485
Ser Thr Ser Lys Thr Thr Ala Thr Ala Ser Lys Thr Ser Thr Thr Thr
    490                 495                 500
Arg Ser Gly Met Ser Leu
505                 510
```

<210> SEQ ID NO 3
<211> LENGTH: 30
<212> TYPE: DNA
<213> ORGANISM: Artificial Sequence
<220> FEATURE:
<223> OTHER INFORMATION: Primer 7258

<400> SEQUENCE: 3
gaatgacttg gttgacgcgt caccagtcac          30

<210> SEQ ID NO 4
<211> LENGTH: 68
<212> TYPE: DNA
<213> ORGANISM: Artificial Sequence
<220> FEATURE:
<223> OTHER INFORMATION: Primer 21401

-continued

<400> SEQUENCE: 4 gggatcatg ataggactag ccatattaat gaagggcata taccacgcct tggacctgcg 60
ttatagcc 68

<210> SEQ ID NO 5
<211> LENGTH: 25
<212> TYPE: DNA
<213> ORGANISM: Artificial Sequence
<220> FEATURE:
<223> OTHER INFORMATION: Primer 107581

<400> SEQUENCE: 5
gcaacgaagc gcccgtggct cgtac 25

<210> SEQ ID NO 6
<211> LENGTH: 88
<212> TYPE: DNA
<213> ORGANISM: Artificial Sequence
<220> FEATURE:
<223> OTHER INFORMATION: Primer FAMGIL

<400> SEQUENCE: 6
cgaagcgacc gtggctcgta ctgccatcta taacatcggc gcgtctgtgc gcggtggcat 60
tgtcgttgct agtcccagca cggataac 88

<210> SEQ ID NO 7
<211> LENGTH: 28
<212> TYPE: DNA
<213> ORGANISM: Artificial Sequence
<220> FEATURE:
<223> OTHER INFORMATION: Primer RAMG1

<400> SEQUENCE: 7
gatggcagta cgagccacgg tcgcttcg 28

<210> SEQ ID NO 8
<211> LENGTH: 75
<212> TYPE: DNA
<213> ORGANISM: Artificial Sequence
<220> FEATURE:
<223> OTHER INFORMATION: PRIMER FAMGIV

<400> SEQUENCE: 8
gtgtcgctgg acttcttcaa gaacctctta ccctactaca gtcgttatca ttgatgccgt 60
gaagactttc gccga 75

<210> SEQ ID NO 9
<211> LENGTH: 21
<212> TYPE: DNA
<213> ORGANISM: PRIMER RAMGVI

<400> SEQUENCE: 9
cttgaagaag tccagcgaca c 21

<210> SEQ ID NO 10
<211> LENGTH: 27
<212> TYPE: DNA
<213> ORGANISM: Artificial Sequence
<220> FEATURE:
<223> OTHER INFORMATION: Primer FG2

<400> SEQUENCE: 10

-continued

```
catccccagg atccttactc agcaatg                                            27

<210> SEQ ID NO 11
<211> LENGTH: 27
<212> TYPE: DNA
<213> ORGANISM: Artificial Sequence
<220> FEATURE:
<223> OTHER INFORMATION: Primer RG2

<400> SEQUENCE: 11
ctcaaacgac tcaccagcct ctagagt                                            27

<210> SEQ ID NO 12
<211> LENGTH: 2602
<212> TYPE: DNA
<213> ORGANISM: ASPERGILLUS NIGER

<400> SEQUENCE: 12
ttcgtcgcct aatgtctcgt ccgttcacaa actgaagagc ttgaagtggc gagatgtctc        60
tgcaggaatt caagctagat gctaagcgat attgcatggc aatatgtgtt gatgcatgtg       120
cttcttcctt cagcttcccc tcgtgcgagt gaggtttggc tataaattga agtggttggt       180
cggggttccg tgaggggctg aagtgcttcc tcccttttag gcgcaactga gagcctgagc       240
ttcatcccca gcatcattac acctcagcaa tgtcgttccg atctctactc gccctgagcg       300
gcctcgtctg cacaggggttg gcaaatgtga tttccaagcg cgcgaccttg gattcatggt       360
tgagcaacga agcgaccgtg gctcgtactg ccatcctgaa taacatcggg gcggacggtg       420
cttgggtgtc gggcgcggac tctggcattg tcgttgctag tcccagcacg gataacccgg       480
actgtatgtt tcgagctcag atttagtatg agtgtgtcat tgattgattg atgctgactg       540
gcgtgtcgtt tgttgtagac ttctacacct ggactcgcga ctctggtctc gtcctcaaga       600
ccctcgtcga tctcttccga aatggagata ccagtctcct ctccaccatt gagaactaca       660
tctccgccca ggcaattgtc cagggtatca gtaacccctc tggtgatctg tccagcggcg       720
ctggtctcgg tgaacccaag ttcaatgtcg atgagactgc ctacactggt tcttggggac       780
ggccgcagcg agatggtccg gctctgagag caactgctat gatcggcttc gggcagtggc       840
tgcttgtatg ttctccaccc ccttgcgtct gatctgtgac atatgtagct gactggtcag       900
gacaatggct acaccagcac cgcaacggac attgtttggc ccctcgttag gaacgacctg       960
tcgtatgtgg ctcaatactg gaaccagaca ggatatggtg tgtttgtttt atttttaaatt      1020 tccaaagatg cgccagcaga gctaacccgc gatcgcagat ctctgggaag aagtcaatgg      1080 ctcgtcttc tttacgattg ctgtgcaaca ccgcgccctt gtcgaaggta gtgccttcgc       1140
gacggccgtc ggctcgtcct gctcctggtg tgattctcag gcacccgaaa ttctctgcta      1200
cctgcagtcc ttctggaccg gcagcttcat tctggccaac ttcgatagca gccgttccgg      1260
caaggacgca aacaccctcc tgggaagcat ccacaccttt gatcctgagg ccgcatgcga      1320
cgactccacc ttccagccct gctccccgcg cgcgctcgcc aaccacaagg aggttgtaga      1380
ctctttccgc tcaatctata ccctcaacga tggtctcagt gacagcgagg ctgttgcggt      1440
gggtcggtac cctgaggaca cgtactacaa cggcaacccg tggttcctgt gcaccttggc      1500
tgccgcagag cagttgtacg atgctctata ccagtgggac aagcagggt cgttggaggt       1560 cacagatgtg tcgctggact tcttcaaggc actgtacagc gatgctgcta ctggcaccta      1620
ctcttcgtcc agttcgactt atagtagcat tgtagatgcc gtgaagactt cgccgatgg      1680 cttcgtctct attgtggtaa gtctacgcta gacaagcgct catgttgaca gagggtgcgt      1740
```

-continued

```
actaacagaa gtaggaaact cacgccgcaa gcaacggctc catgtccgag caatacgaca    1800
agtctgatgg cgagcagctt tccgctcgcg acctgacctg gtcttatgct gctctgctga    1860
ccgccaacaa ccgtcgtaac tccgtcgtgc ctgcttcttg gggcgagacc tctgccagca    1920
gcgtgcccgg cacctgtgcg gccacatctg ccattggtac ctacagcagt gtgactgtca    1980
cctcgtggcc gagtatcgtg gctactggcg gcaccactac gacggctacc cccactggat    2040
ccggcagcgt gacctcgacc agcaagacca ccgcgactgc tagcaagacc agcaccagta    2100
cgtcatcaac ctcctgtacc actcccaccg ccgtggctgt gactttcgat ctgacagcta    2160
ccaccaccta cggcgagaac atctacctgg tcggatcgat ctctcagctg ggtgactggg    2220
aaaccagcga cggcatagct ctgagtgctg acaagtacac ttccagcgac ccgctctggt    2280
atgtcactgt gactctgccg gctggtgagt cgtttgagta caagtttatc cgcattgaga    2340
gcgatgactc cgtggagtgg gagagtgatc caaccgaga atacaccgtt cctcaggcgt     2400
gcggaacgtc gaccgcgacg gtgactgaca cctggcggtg acaatcaatc catttcgcta    2460
tagttaaagg atggggatga gggcaattgg ttatatgatc atgtatgtag tgggtgtgca    2520
taatagtagt gaaatggaag ccaagtcatg tgattgtaat cgaccgacgg aattgaggat    2580
atccggaaat acagacaccg gg                                              2602
```

<210> SEQ ID NO 13
<211> LENGTH: 640
<212> TYPE: PRT
<213> ORGANISM: ASPERGILLUS NIGER

<400> SEQUENCE: 13

```
Met Ser Phe Arg Ser Leu Leu Ala Leu Ser Gly Leu Val Cys Thr Gly
  1               5                  10                  15

Leu Ala Asn Val Ile Ser Lys Arg Ala Thr Leu Asp Ser Trp Leu Ser
             20                  25                  30

Asn Glu Ala Thr Val Ala Arg Thr Ala Ile Leu Asn Asn Ile Gly Ala
         35                  40                  45

Asp Gly Ala Trp Val Ser Gly Ala Asp Ser Gly Ile Val Ala Ser
     50                  55                  60

Pro Ser Thr Asp Asn Pro Asp Tyr Phe Tyr Thr Trp Thr Arg Asp Ser
 65                  70                  75                  80

Gly Leu Val Leu Lys Thr Leu Val Asp Leu Phe Arg Asn Gly Asp Thr
                 85                  90                  95

Ser Leu Leu Ser Thr Ile Glu Asn Tyr Ile Ser Ala Gln Ala Ile Val
            100                 105                 110

Gln Gly Ile Ser Asn Pro Ser Gly Asp Leu Ser Ser Gly Ala Gly Leu
        115                 120                 125

Gly Glu Pro Lys Phe Asn Val Asp Glu Thr Ala Tyr Thr Gly Ser Trp
    130                 135                 140

Gly Arg Pro Gln Arg Asp Gly Pro Ala Leu Arg Ala Thr Ala Met Ile
145                 150                 155                 160

Gly Phe Gly Gln Trp Leu Leu Asp Asn Gly Tyr Thr Ser Thr Ala Thr
                165                 170                 175

Asp Ile Val Trp Pro Leu Val Arg Asn Asp Leu Ser Tyr Val Ala Gln
            180                 185                 190

Tyr Trp Asn Gln Thr Gly Tyr Asp Leu Trp Glu Glu Val Asn Gly Ser
        195                 200                 205

Ser Phe Phe Thr Ile Ala Val Gln His Arg Ala Leu Val Glu Gly Ser
```

```
              210                 215                 220
Ala Phe Ala Thr Ala Val Gly Ser Ser Cys Ser Trp Cys Asp Ser Gln
225                 230                 235                 240

Ala Pro Glu Ile Leu Cys Tyr Leu Gln Ser Phe Trp Thr Gly Ser Phe
                245                 250                 255

Ile Leu Ala Asn Phe Asp Ser Ser Arg Ser Gly Lys Asp Ala Asn Thr
                260                 265                 270

Leu Leu Gly Ser Ile His Thr Phe Asp Pro Glu Ala Ala Cys Asp Asp
                275                 280                 285

Ser Thr Phe Gln Pro Cys Ser Pro Arg Ala Leu Ala Asn His Lys Glu
    290                 295                 300

Val Val Asp Ser Phe Arg Ser Ile Tyr Thr Leu Asn Asp Gly Leu Ser
305                 310                 315                 320

Asp Ser Glu Ala Val Ala Val Gly Arg Tyr Pro Glu Asp Thr Tyr Tyr
                325                 330                 335

Asn Gly Asn Pro Trp Phe Leu Cys Thr Leu Ala Ala Ala Glu Gln Leu
                340                 345                 350

Tyr Asp Ala Leu Tyr Gln Trp Asp Lys Gln Gly Ser Leu Glu Val Thr
                355                 360                 365

Asp Val Ser Leu Asp Phe Phe Lys Ala Leu Tyr Ser Asp Ala Ala Thr
                370                 375                 380

Gly Thr Tyr Ser Ser Ser Ser Thr Tyr Ser Ser Ile Val Asp Ala
385                 390                 395                 400

Val Lys Thr Phe Ala Asp Gly Phe Val Ser Ile Val Glu Thr His Ala
                405                 410                 415

Ala Ser Asn Gly Ser Met Ser Glu Gln Tyr Asp Lys Ser Asp Gly Glu
                420                 425                 430

Gln Leu Ser Ala Arg Asp Leu Thr Trp Ser Tyr Ala Ala Leu Leu Thr
                435                 440                 445

Ala Asn Asn Arg Arg Asn Ser Val Val Pro Ala Ser Trp Gly Glu Thr
                450                 455                 460

Ser Ala Ser Ser Val Pro Gly Thr Cys Ala Ala Thr Ser Ala Ile Gly
465                 470                 475                 480

Thr Tyr Ser Ser Val Thr Val Thr Ser Trp Pro Ser Ile Val Ala Thr
                485                 490                 495

Gly Gly Thr Thr Thr Thr Ala Thr Pro Thr Gly Ser Gly Ser Val Thr
                500                 505                 510

Ser Thr Ser Lys Thr Thr Ala Thr Ala Ser Lys Thr Ser Thr Ser Thr
                515                 520                 525

Ser Ser Thr Ser Cys Thr Thr Pro Thr Ala Val Ala Val Thr Phe Asp
                530                 535                 540

Leu Thr Ala Thr Thr Tyr Gly Glu Asn Ile Tyr Leu Val Gly Ser
545                 550                 555                 560

Ile Ser Gln Leu Gly Asp Trp Glu Thr Ser Asp Gly Ile Ala Leu Ser
                565                 570                 575

Ala Asp Lys Tyr Thr Ser Asp Pro Leu Trp Tyr Val Thr Val Thr
                580                 585                 590

Leu Pro Ala Gly Glu Ser Phe Glu Tyr Lys Phe Ile Arg Ile Glu Ser
                595                 600                 605

Asp Asp Ser Val Glu Trp Glu Ser Asp Pro Asn Arg Glu Tyr Thr Val
                610                 615                 620

Pro Gln Ala Cys Gly Thr Ser Thr Ala Thr Val Thr Asp Thr Trp Arg
625                 630                 635                 640
```

<210> SEQ ID NO 14
<211> LENGTH: 43
<212> TYPE: DNA
<213> ORGANISM: Artificial Sequence
<220> FEATURE:
<223> OTHER INFORMATION: primer K1-T2X n at positions 22 and 23 is a or
      g or c or t

<400> SEQUENCE: 14
atgtgatttc caagcgcgcg vnnttggatt catggttgag caa                       43

<210> SEQ ID NO 15
<211> LENGTH: 43
<212> TYPE: DNA
<213> ORGANISM: Artificial Sequence
<220> FEATURE:
<223> OTHER INFORMATION: primer Hk1-N9X n at positions 22 and 23 is a or
      g or c or t

<400> SEQUENCE: 15
ccttggattc atggttgagc vnngaagcga ccgtggctcg tac                       43

<210> SEQ ID NO 16
<211> LENGTH: 43
<212> TYPE: DNA
<213> ORGANISM: Artificial Sequence
<220> FEATURE:
<223> OTHER INFORMATION: primer Hk1-A11X n at positions 22 and 23 is a
      or g or c or t

<400> SEQUENCE: 16
attcatggtt gagcaacgaa vnnaccgtgg ctcgtactgc cat                       43

<210> SEQ ID NO 17
<211> LENGTH: 43
<212> TYPE: DNA
<213> ORGANISM: Artificial Sequence
<220> FEATURE:
<223> OTHER INFORMATION: primer Hk1-L66X n at positions 22 and 23 is a
      or g or c or t

<400> SEQUENCE: 17
tcctcaagac cctcgtcgat vnnttccgaa atggagatac cag                       43

<210> SEQ ID NO 18
<211> LENGTH: 43
<212> TYPE: DNA
<213> ORGANISM: Artificial Sequence
<220> FEATURE:
<223> OTHER INFORMATION: primer Hk1-S386X n at positions 22 and 23 is a
      or g or c or t

<400> SEQUENCE: 18
ctttcgccga tggcttcgtc vnnattgtgg aaactcacgc cgc                       43

<210> SEQ ID NO 19
<211> LENGTH: 43
<212> TYPE: DNA
<213> ORGANISM: Artificial Sequence
<220> FEATURE:
<223> OTHER INFORMATION: primer Hk1-E389X n at positions 22 and 23 is a
      or g or c or t

<400> SEQUENCE: 19
atggcttcgt ctctattgtg vnnactcacg ccgcaagcaa cgg                       43

<210> SEQ ID NO 20
<211> LENGTH: 43
<212> TYPE: DNA
<213> ORGANISM: Artificial Sequence
<220> FEATURE:
<223> OTHER INFORMATION: primer Hk1-T390X n at positions 22 and 23 are a
      or g or c

<400> SEQUENCE: 20
gcttcgtctc tattgtggaa vnncacgccg caagcaacgg ctc                43

<210> SEQ ID NO 21
<211> LENGTH: 43
<212> TYPE: DNA
<213> ORGANISM: Artificial Sequence
<220> FEATURE:
<223> OTHER INFORMATION: primer Hk1-A393X n at positions 22 and 23 is a
      or g or c or t

<400> SEQUENCE: 21
ctattgtgga aactcacgcc vnnagcaacg gctccatgtc cga                43

<210> SEQ ID NO 22
<211> LENGTH: 43
<212> TYPE: DNA
<213> ORGANISM: Artificial Sequence
<220> FEATURE:
<223> OTHER INFORMATION: primer Hk1-S394X n at positions 22 and 23 is a
      or g or c or t

<400> SEQUENCE: 22
ttgtggaaac tcacgccgca vnnaacggct ccatgtccga gca                43

<210> SEQ ID NO 23
<211> LENGTH: 43
<212> TYPE: DNA
<213> ORGANISM: Artificial Sequence
<220> FEATURE:
<223> OTHER INFORMATION: primer Hk1-395X n at positions 22 and 23 is a
      or g or c or t

<400> SEQUENCE: 23
tggaaactca cgccgcaagc vnnggctcca tgtccgagca ata                43

<210> SEQ ID NO 24
<211> LENGTH: 43
<212> TYPE: DNA
<213> ORGANISM: Artificial Sequence
<220> FEATURE:
<223> OTHER INFORMATION: primer Hk1-G396X n at positions 22 and 23 is a
      or g or c or t

<400> SEQUENCE: 24
aaactcacgc cgcaagcaac vnntccatgt ccgagcaata cga                43

<210> SEQ ID NO 25
<211> LENGTH: 43
<212> TYPE: DNA
<213> ORGANISM: Artificial Sequence
<220> FEATURE:
<223> OTHER INFORMATION: primer Hk1-K404X n at positions 22 and 23 is a
      or g or c or t

<400> SEQUENCE: 25
ccatgtccga gcaatacgac vnntctgatg gcgagcagct ttc                43

<210> SEQ ID NO 26
<211> LENGTH: 43
<212> TYPE: DNA
<213> ORGANISM: Artificial Sequence
<220> FEATURE:
<223> OTHER INFORMATION: primer Hk1-D406X n at positions 22 and 23 is a
      or g or c or t

<400> SEQUENCE: 26
ccgagcaata cgacaagtct vnnggcgagc agctttccgc tcg                43

<210> SEQ ID NO 27
<211> LENGTH: 43
<212> TYPE: DNA
<213> ORGANISM: Artificial Sequence
<220> FEATURE:
<223> OTHER INFORMATION: primer Hk1-E408X n at positions 22 and 23 is a
      or g or c or t

<400> SEQUENCE: 27
aatacgacaa gtctgatggc vnncagcttt ccgctcgcga cct                43

<210> SEQ ID NO 28
<211> LENGTH: 42
<212> TYPE: DNA
<213> ORGANISM: Artificial Sequence
<220> FEATURE:
<223> OTHER INFORMATION: primer Hk1-L410X n at positions 22 and 23 is a
      or g or c or t

<400> SEQUENCE: 28
acaagtctga tggcgagcag vnntccgctc gcgacctgac ct                 42

<210> SEQ ID NO 29
<211> LENGTH: 43
<212> TYPE: DNA
<213> ORGANISM: Artificial Sequence
<220> FEATURE:
<223> OTHER INFORMATION: primer Hk1-L423X n at positions 22 and 23 is a
      or g or c or t

<400> SEQUENCE: 29
cctggtctta tgctgctctg vnnaccgcca acaaccgtcg taa                43

<210> SEQ ID NO 30
<211> LENGTH: 44
<212> TYPE: DNA
<213> ORGANISM: Artificial Sequence
<220> FEATURE:
<223> OTHER INFORMATION: primer Hk1-N426X n at positions 22 and 23 is a
      or g or c or t

<400> SEQUENCE: 30
atgctgctct gctgaccgcc vnnaaccgtc gtaactccgt cgtg               44

<210> SEQ ID NO 31
<211> LENGTH: 44
<212> TYPE: DNA
<213> ORGANISM: Artificial Sequence
<220> FEATURE:
<223> OTHER INFORMATION: primer Hk1-N427X n at positions 22 and 23 is a
      or g or c or t

<400> SEQUENCE: 31
ctgctctgct gaccgccaac vnncgtcgta actccgtcgt gcct               44

<210> SEQ ID NO 32

<210> SEQ ID NO 32
<211> LENGTH: 46
<212> TYPE: DNA
<213> ORGANISM: Artificial Sequence
<220> FEATURE:
<223> OTHER INFORMATION: primer Hk1-Y402X n at positions 21 and 22 is a
      or g or c or t

<400> SEQUENCE: 32
acggctccat gtccgagcaa nncgacaagt ctgatggcga gcagct                46

<210> SEQ ID NO 33
<211> LENGTH: 41
<212> TYPE: DNA
<213> ORGANISM: Artificial Sequence
<220> FEATURE:
<223> OTHER INFORMATION: primer Hk2-L234X-sense n at positions 20 and 21
      is a or g or c or t

<400> SEQUENCE: 33
ctggaccggc agcttcattn nkgccaactt cgatagcagc c                     41

<210> SEQ ID NO 34
<211> LENGTH: 42
<212> TYPE: DNA
<213> ORGANISM: Artificial Sequence
<220> FEATURE:
<223> OTHER INFORMATION: primer Hk2-A235S-antisense

<400> SEQUENCE: 34
gaacggctgc tatcgaagtt agacagaatg aagctgccgg tc                    42

<210> SEQ ID NO 35
<211> LENGTH: 41
<212> TYPE: DNA
<213> ORGANISM: Artificial Sequence
<220> FEATURE:
<223> OTHER INFORMATION: primer Hk2-NF237X-sense n at position 20 is a
      or g or c or t

<400> SEQUENCE: 35
cagcttcatt ctggccaacn atgatagcag ccgttccggc a                     41

<210> SEQ ID NO 36
<211> LENGTH: 42
<212> TYPE: DNA
<213> ORGANISM: Artificial Sequence
<220> FEATURE:
<223> OTHER INFORMATION: primer Hk2-D235T-antisense

<400> SEQUENCE: 36
ccttgccgga acggctgcta gtgaagttgg ccagaatgaa gc                    42

<210> SEQ ID NO 37
<211> LENGTH: 42
<212> TYPE: DNA
<213> ORGANISM: Artificial Sequence
<220> FEATURE:
<223> OTHER INFORMATION: primer Hk2-D238S-antisense

<400> SEQUENCE: 37
ccttgccgga acggctgcta gagaagttgg ccagaatgaa gc                    42

<210> SEQ ID NO 38
<211> LENGTH: 42
<212> TYPE: DNA
<213> ORGANISM: Artificial Sequence
<220> FEATURE:

<223> OTHER INFORMATION: primer Hk2-S239X-sense n at positions 21 and 22
    is a or g or c or t

<400> SEQUENCE: 38
tcattctggc caacttcgat nncagccgtt ccggcaagga cg            42

<210> SEQ ID NO 39
<211> LENGTH: 42
<212> TYPE: DNA
<213> ORGANISM: Artificial Sequence
<220> FEATURE:
<223> OTHER INFORMATION: primer Hk2-S240G-antisense

<400> SEQUENCE: 39
ttgcgtcctt gccggaacga ccgctatcga agttggccag aa            42

<210> SEQ ID NO 40
<211> LENGTH: 41
<212> TYPE: DNA
<213> ORGANISM: Artificial Sequence
<220> FEATURE:
<223> OTHER INFORMATION: primer Hk2-S242X-antisense n at position 22 is
    a or g or c or t

<400> SEQUENCE: 40
gggtgtttgc gtccttgcca knacggctgc tatcgaagtt g            41

<210> SEQ ID NO 41
<211> LENGTH: 41
<212> TYPE: DNA
<213> ORGANISM: Artificial Sequence
<220> FEATURE:
<223> OTHER INFORMATION: primer Hk2-G243X-antisense n at position 22 is
    a or g or c or t

<400> SEQUENCE: 41
ggagggtgtt tgcgtcctta knggaacggc tgctatcgaa g            41

<210> SEQ ID NO 42
<211> LENGTH: 41
<212> TYPE: DNA
<213> ORGANISM: Artificial Sequence
<220> FEATURE:
<223> OTHER INFORMATION: primer Hk2-K244R-sense

<400> SEQUENCE: 42
cgatagcagc cgttccggca gagacgcaaa caccctcctg g            41

<210> SEQ ID NO 43
<211> LENGTH: 41
<212> TYPE: DNA
<213> ORGANISM: Artificial Sequence
<220> FEATURE:
<223> OTHER INFORMATION: primer Hk2-T310V-antisense

<400> SEQUENCE: 43
acgggttgcc gttgtagtaa acgtcctcag ggtaccgacc c            41

<210> SEQ ID NO 44
<211> LENGTH: 41
<212> TYPE: DNA
<213> ORGANISM: Artificial Sequence
<220> FEATURE:
<223> OTHER INFORMATION: primer Hk2-T310S-antisense

<400> SEQUENCE: 44
acgggttgcc gttgtagtaa gagtcctcag ggtaccgacc c                          41

<210> SEQ ID NO 45
<211> LENGTH: 41
<212> TYPE: DNA
<213> ORGANISM: Artificial Sequence
<220> FEATURE:
<223> OTHER INFORMATION: primer Hk2-Y311N-sense

<400> SEQUENCE: 45
tcggtaccct gaggacacga attacaacgg caacccgtgg t                          41

<210> SEQ ID NO 46
<211> LENGTH: 41
<212> TYPE: DNA
<213> ORGANISM: Artificial Sequence
<220> FEATURE:
<223> OTHER INFORMATION: Hk2-Y312Q-antisense

<400> SEQUENCE: 46
ggaaccacgg gttgccgttt tggtacgtgt cctcagggta c                          41

<210> SEQ ID NO 47
<211> LENGTH: 41
<212> TYPE: DNA
<213> ORGANISM: Artificial Sequence
<220> FEATURE:
<223> OTHER INFORMATION: primer Hk2-Y312N-antisense

<400> SEQUENCE: 47
ggaaccacgg gttgccgtta ttgtacgtgt cctcagggta c                          41

<210> SEQ ID NO 48
<211> LENGTH: 41
<212> TYPE: DNA
<213> ORGANISM: Artificial Sequence
<220> FEATURE:
<223> OTHER INFORMATION: primer Hk2-N313T-sense

<400> SEQUENCE: 48
ccctgaggac acgtactaca ctggcaaccc gtggttcctg t                          41

<210> SEQ ID NO 49
<211> LENGTH: 41
<212> TYPE: DNA
<213> ORGANISM: Artificial Sequence
<220> FEATURE:
<223> OTHER INFORMATION: primer Hk2-N313S-sense

<400> SEQUENCE: 49
ccctgaggac acgtactact ctggcaaccc gtggttcctg t                          41

<210> SEQ ID NO 50
<211> LENGTH: 41
<212> TYPE: DNA
<213> ORGANISM: Artificial Sequence
<220> FEATURE:
<223> OTHER INFORMATION: primer Hk2-N313G-sense

<400> SEQUENCE: 50
ccctgaggac acgtactacg gtggcaaccc gtggttcctg t                          41

<210> SEQ ID NO 51
<211> LENGTH: 41
<212> TYPE: DNA
<213> ORGANISM: Artificial Sequence
<220> FEATURE:
<223> OTHER INFORMATION: primer Hk2-N315Q-antisense

<400> SEQUENCE: 51
aggtgcacag gaaccacggt tggccgttgt agtacgtgtc c                                41

<210> SEQ ID NO 52
<211> LENGTH: 41
<212> TYPE: DNA
<213> ORGANISM: Artificial Sequence
<220> FEATURE:
<223> OTHER INFORMATION: primer Hk2-N315E-antisense

<400> SEQUENCE: 52
aggtgcacag gaaccacggt tcgccgttgt agtacgtgtc c                                41

<210> SEQ ID NO 53
<211> LENGTH: 41
<212> TYPE: DNA
<213> ORGANISM: Artificial Sequence
<220> FEATURE:
<223> OTHER INFORMATION: primer Hk2-N315R-antisense

<400> SEQUENCE: 53
aggtgcacag gaaccacggt ctgccgttgt agtacgtgtc c                                41

<210> SEQ ID NO 54
<211> LENGTH: 41
<212> TYPE: DNA
<213> ORGANISM: Artificial Sequence
<220> FEATURE:
<223> OTHER INFORMATION: primer Hk2-F318Y-antisense

<400> SEQUENCE: 54
cggcagccaa ggtgcacaga taccacgggt tgccgttgta g                                41

<210> SEQ ID NO 55
<211> LENGTH: 41
<212> TYPE: DNA
<213> ORGANISM: Artificial Sequence
<220> FEATURE:
<223> OTHER INFORMATION: primer Hk2-Q409P-sense

<400> SEQUENCE: 55
cgacaagtct gatggcgagc cactttccgc tcgcgacctg a                                41

<210> SEQ ID NO 56
<211> LENGTH: 41
<212> TYPE: DNA
<213> ORGANISM: Artificial Sequence
<220> FEATURE:
<223> OTHER INFORMATION: primer Hk3-D336X-sense n at positions 20 and 21
      is a or g or c or t

<400> SEQUENCE: 56
cgatgctcta taccagtggn nkaagcaggg gtcgttggag g                                41

<210> SEQ ID NO 57
<211> LENGTH: 41
<212> TYPE: DNA
<213> ORGANISM: Artificial Sequence
<220> FEATURE:
<223> OTHER INFORMATION: primer Hk3-K337X-sense n at positions 20 and 21
      is a or g or c or t

<400> SEQUENCE: 57
tgctctatac cagtgggacn nkcaggggtc gttggaggtc a                              41

<210> SEQ ID NO 58
<211> LENGTH: 41
<212> TYPE: DNA
<213> ORGANISM: Artificial Sequence
<220> FEATURE:
<223> OTHER INFORMATION: primer Hk3-Q338X-antisense n at positions 21
    and 22 is a or g or c or t

<400> SEQUENCE: 58
ctgtgacctc caacgacccg nncttgtccc actggtatag a                              41

<210> SEQ ID NO 59
<211> LENGTH: 41
<212> TYPE: DNA
<213> ORGANISM: Artificial Sequence
<220> FEATURE:
<223> OTHER INFORMATION: primer Hk3-G339X-sense n at position 20 is a or
    g or c or t

<400> SEQUENCE: 59
ataccagtgg gacaagcagn cutcgttgga ggtcacagat g                              41

<210> SEQ ID NO 60
<211> LENGTH: 41
<212> TYPE: DNA
<213> ORGANISM: Artificial Sequence
<220> FEATURE:
<223> OTHER INFORMATION: primer Hk3-S340X'-antisense n at position 21 is
    a or g or c or t

<400> SEQUENCE: 60
acacatctgt gacctccaaa ntccctgct tgtcccactg g                               41

<210> SEQ ID NO 61
<211> LENGTH: 41
<212> TYPE: DNA
<213> ORGANISM: Artificial Sequence
<220> FEATURE:
<223> OTHER INFORMATION: primer Hk3-S340X"-antisense n at position 21 is
    a or g or c or t

<400> SEQUENCE: 61
acacatctgt gacctccaaa ncccctgct tgtcccactg g                               41

<210> SEQ ID NO 62
<211> LENGTH: 41
<212> TYPE: DNA
<213> ORGANISM: Artificial Sequence
<220> FEATURE:
<223> OTHER INFORMATION: primer Hk3-L341X-sense n at position 20 is a or
    g or c or t

<400> SEQUENCE: 62
gtgggacaag cagggtcgn uugaggtcac agatgtgtcg c                               41

<210> SEQ ID NO 63
<211> LENGTH: 41
<212> TYPE: DNA
<213> ORGANISM: Artificial Sequence
<220> FEATURE:
<223> OTHER INFORMATION: primer Hk3-K352Q-sense

<400> SEQUENCE: 63
tgtgtcgctg gacttcttcc aagcactgta cagcgatgct g                              41

<210> SEQ ID NO 64
<211> LENGTH: 41
<212> TYPE: DNA
<213> ORGANISM: Artificial Sequence
<220> FEATURE:
<223> OTHER INFORMATION: primer Hk3-K352R-sense

<400> SEQUENCE: 64
tgtgtcgctg gacttcttca gagcactgta cagcgatgct g                41

<210> SEQ ID NO 65
<211> LENGTH: 41
<212> TYPE: DNA
<213> ORGANISM: Artificial Sequence
<220> FEATURE:
<223> OTHER INFORMATION: primer Hk3-A352D-antisense

<400> SEQUENCE: 65
tagcagcatc gctgtacaga tccttgaaga agtccagcga c                41

<210> SEQ ID NO 66
<211> LENGTH: 41
<212> TYPE: DNA
<213> ORGANISM: Artificial Sequence
<220> FEATURE:
<223> OTHER INFORMATION: primer HK3-A353S-antisense

<400> SEQUENCE: 66
tagcagcatc gctgtacaga gacttgaaga agtccagcga c                41

<210> SEQ ID NO 67
<211> LENGTH: 42
<212> TYPE: DNA
<213> ORGANISM: Artificial Sequence
<220> FEATURE:
<223> OTHER INFORMATION: primer Hk3-S356P-sense

<400> SEQUENCE: 67
acttcttcaa ggcactgtac ccagatgctg ctactggcac ct               42

<210> SEQ ID NO 68
<211> LENGTH: 43
<212> TYPE: DNA
<213> ORGANISM: Artificial Sequence
<220> FEATURE:
<223> OTHER INFORMATION: primer Hk3-S356N-sense

<400> SEQUENCE: 68
acttcttcaa ggcactgtac aaugatgctg ctactggcac cta              43

<210> SEQ ID NO 69
<211> LENGTH: 43
<212> TYPE: DNA
<213> ORGANISM: Artificial Sequence
<220> FEATURE:
<223> OTHER INFORMATION: primer Hk3-S356D-sense

<400> SEQUENCE: 69
acttcttcaa ggcactgtac gaugatgctg ctactggcac cta              43

<210> SEQ ID NO 70
<211> LENGTH: 43
<212> TYPE: DNA
<213> ORGANISM: Artificial Sequence
<220> FEATURE:
<223> OTHER INFORMATION: primer Hk3-D357S-antisense

```
<400> SEQUENCE: 70
gagtaggtgc cagtagcagc agagctgtac agtgccttga aga                43

<210> SEQ ID NO 71
<211> LENGTH: 41
<212> TYPE: DNA
<213> ORGANISM: Artificial Sequence
<220> FEATURE:
<223> OTHER INFORMATION: primer Hk3-A359S-sense

<400> SEQUENCE: 71
ggcactgtac agcgatgctt ctactggcac ctactcttcg t                  41

<210> SEQ ID NO 72
<211> LENGTH: 41
<212> TYPE: DNA
<213> ORGANISM: Artificial Sequence
<220> FEATURE:
<223> OTHER INFORMATION: primer Hk3-T360V-antisense

<400> SEQUENCE: 72
tggacgaaga gtaggtgcca acagcagcat cgctgtacag t                  41

<210> SEQ ID NO 73
<211> LENGTH: 43
<212> TYPE: DNA
<213> ORGANISM: Artificial Sequence
<220> FEATURE:
<223> OTHER INFORMATION: primer Hk3-G361X-sense n at position 21 is a or
      g or c or t

<400> SEQUENCE: 73
tgtacagcga tgctgctact nctacctact cttcgtccag ttc                43

<210> SEQ ID NO 74
<211> LENGTH: 42
<212> TYPE: DNA
<213> ORGANISM: Artificial Sequence
<220> FEATURE:
<223> OTHER INFORMATION: primer Hk3-T362R-antisense

<400> SEQUENCE: 74
gtcgaactgg acgaagagta tctgccagta gcagcatcgc tg                 42

<210> SEQ ID NO 75
<211> LENGTH: 42
<212> TYPE: DNA
<213> ORGANISM: Artificial Sequence
<220> FEATURE:
<223> OTHER INFORMATION: primer Hk3-S364X-sense n at positions 20 and 21
      is a or g or c or t

<400> SEQUENCE: 75
tgctgctact ggcacctacn nktcgtccag ttcgacttat ag                 42

<210> SEQ ID NO 76
<211> LENGTH: 42
<212> TYPE: DNA
<213> ORGANISM: Artificial Sequence
<220> FEATURE:
<223> OTHER INFORMATION: primer Hk3-S365X-sense n at positions 20 and 21
      is a or g or c or t

<400> SEQUENCE: 76
tgctactggc acctactctn nktccagttc gacttatagt ag                 42
```

```
<210> SEQ ID NO 77
<211> LENGTH: 42
<212> TYPE: DNA
<213> ORGANISM: Artificial Sequence
<220> FEATURE:
<223> OTHER INFORMATION: primer Hk3-S366T-antisense

<400> SEQUENCE: 77
atgctactat aagtcgaact agtcgaagag taggtgccag ta                42

<210> SEQ ID NO 78
<211> LENGTH: 42
<212> TYPE: DNA
<213> ORGANISM: Artificial Sequence
<220> FEATURE:
<223> OTHER INFORMATION: primer Hk3-S368X-antisense n at position 23 is
      a or g or c or t

<400> SEQUENCE: 78
tctacaatgc tactataagt agnactggac gaagagtagg tg                42

<210> SEQ ID NO 79
<211> LENGTH: 43
<212> TYPE: DNA
<213> ORGANISM: Artificial Sequence
<220> FEATURE:
<223> OTHER INFORMATION: primer Hk3-T369X-sense n at positions 20 and 21
      is a or g or c or t

<400> SEQUENCE: 79
ctactcttcg tccagttcgn nktatagtag cattgtagat gcc               43

<210> SEQ ID NO 80
<211> LENGTH: 43
<212> TYPE: DNA
<213> ORGANISM: Artificial Sequence
<220> FEATURE:
<223> OTHER INFORMATION: primer Hk3-S371X-antisense n at position 23 is
      a or g or c or t

<400> SEQUENCE: 80
ttcacggcat ctacaatgct atnataagtc gaactggacg aag               43

<210> SEQ ID NO 81
<211> LENGTH: 43
<212> TYPE: DNA
<213> ORGANISM: Artificial Sequence
<220> FEATURE:
<223> OTHER INFORMATION: primer Hk3-S372X-sense n at positions 21 and 22
      is a or g or c or t

<400> SEQUENCE: 81
cgtccagttc gacttatagt nntattgtag atgccgtgaa gac               43
```